United States Patent [19]

Ishida et al.

[11] 4,097,665
[45] Jun. 27, 1978

[54] DIACYLNUCLEOSIDES AND PROCESS FOR PREPARING THE SAME

[75] Inventors: Torao Ishida; Minoru Akiyama; Daikichi Nishimura; Hiroshi Hayashi, all of Fuji; Yoshio Sakurai, Mitaka; Shigeru Tsukagoshi, Tokyo, all of Japan

[73] Assignee: Asahi Kasei Kogyo Kabushiki Kaisha, Osaka, Japan

[21] Appl. No.: 634,706

[22] Filed: Nov. 24, 1975

[30] Foreign Application Priority Data

Nov. 22, 1974   Japan ................................ 49-133556

[51] Int. Cl.² .......................................... C07H 19/08
[52] U.S. Cl. ........................................ 536/23; 424/180; 536/22
[58] Field of Search .................. 260/211.5 R; 536/23, 536/22

[56] References Cited

U.S. PATENT DOCUMENTS

| | | | |
|---|---|---|---|
| 3,300,478 | 1/1967 | Wechter et al. | 260/211.5 R |
| 3,309,359 | 3/1967 | Duschinsky et al. | 260/211.5 R |
| 3,317,512 | 5/1967 | Wechter | 260/211.5 R |
| 3,457,253 | 7/1969 | Wechter | 260/211.5 R |
| 3,709,874 | 1/1973 | Moffatt et al. | 260/211.5 R |
| 3,847,898 | 11/1974 | Kelly et al. | 260/211.5 R |
| 3,864,483 | 2/1975 | Stein et al. | 260/211.5 R |
| 3,894,000 | 7/1975 | Wechter et al. | 260/211.5 R |
| 3,920,630 | 11/1975 | Wechter et al. | 260/211.5 R |
| 3,998,807 | 12/1976 | Moffatt | 536/23 |

*Primary Examiner* — Johnnie R. Brown
*Attorney, Agent, or Firm* — Sughrue, Rothwell, Mion, Zinn and Macpeak

[57] ABSTRACT

Compounds represented by formula (I)

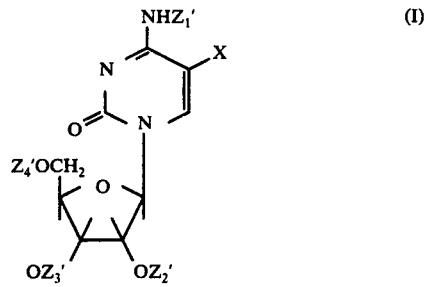

wherein one of $Z_1'$, $Z_2'$, $Z_3'$ and $Z_4'$ represents R, another one of $Z_1'$, $Z_2'$, $Z_3'$ and $Z_4'$ represents Z, and the remaining two moieties of $Z_1'$, $Z_2'$, $Z_3'$ and $Z_4'$ represents a hydrogen atom and/or a protective group, one of R and Z represents $A_1$ and the other represents $A_2$, $A_1$ being an acyl group having 14 to 22 carbon atoms which does not contain a carboxylic group and $A_2$ being an acyl group having 2 to 14 carbon atoms and having one carboxyl group, X represents a hydrogen atom or a halogen atom (hereinafter referred to as Compound Ia); a 2,2'-anhydro product of Compound Ia wherein $Z_2'$ represents a hydrogen atom (hereinafter referred to as Compound Ib); an arabinosylation product of Compound Ia (hereinafter referred to as Compound Ic); a deamination product of Compound Ia (hereinafter referred to as Compound Id); a 2'-deoxy product of Compound Id wherein $Z_2'$ represents a hydrogen atom (hereinafter referred to as Compound Ie); a salt of Compound Ia, Ib, Ic, or Id or Ie having an $A_2$ group with a base (hereinafter referred to as Compound If); and a salt of Compound Ia, Ib or Ic wherein $Z_1'$ represents a hydrogen atom with an acid (hereinafter referred to as Compound Ih); and processes for preparing the same.

8 Claims, No Drawings

DIACYLNUCLEOSIDES AND PROCESS FOR PREPARING THE SAME

BACKGROUND OF THE INVENTION

1. Field of the Invention

This invention relates to compounds useful as antileukemia, e.g., in mice, agents which are water-soluble and which have stable antileukemia activity in a living body, e.g., in mice, intermediates for the preparation of such antileukemia, e.g., in mice, agents and a process for preparing the same.

2. Description of the Prior Art

Cytidine, 5-halocytidine, 2,2'-anhydrocytidine, 2,2'-anhydro-5-halocytidine, cytosine arabinoside, 5-halocytosine arabinoside, uridine, 5-halouridine, 2'-deoxyuridine and 2'-deoxy-5-halouridine are known in the art and commercially available. Since there are many prior art references teaching various preparations for these compounds, they can easily be prepared in accordance with the processes described in the prior art. These well known processes are described in A. M. Michelson, *The Chemistry of Nucleosides and Nucleotides*, published by Academic Press (1963); and Zorback and Tipson, *Synthetic Procedure in Nucleic Acid Chemistry*, published by John Wiley & Sons (1968).

Monoacyl compounds of cytosine derivatives and diacyl compounds of cytosine derivatives having the same acyl groups are disclosed in U.S. Pat. Nos. 3,309,359, 3,317,512 and 3,457,253; *Journal of Medicinal Chemistry* Vol. 15, page 116; *Biochemical Pharmacology*, Vol. 21, page 465; *Cancer Chemotherapy Report*, Part 1, Vol. 58, page 451; Japanese Patent Application Laid Open Nos. 5,997/72, 16,481/72, 132,084/74 and 18,482/75, etc. Of these known compounds, the acyl derivatives (which have been reported to be markedly effective for improving the survival ratio of L-1210 leukemia mice) are water-insoluble while, in contrast, water-soluble acyl derivatives are not effective for improving the survival ratio of L-1210 leukemia mice.

Monoacyl compounds of uracyl derivatives having 12 or less carbon atoms in the acyl moiety thereof and diacyl compounds of uracyl derivatives having the same acyl groups of 2 to 18 carbon atoms have been reported in *Biochemical Pharmacology*, Vol. 14, page 1605. These well-known compounds are effective against adenocarcinoma 755 but are not effective for improving the survival ratio of L-1210 leukemia mice.

SUMMARY OF THE INVENTION

A primary object of this invention is to provide novel compounds represented by the following formula (I):

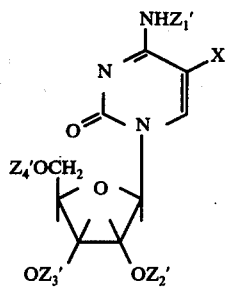

wherein one of $Z_1'$, $Z_2'$, $Z_3'$ and $Z_4'$ represents R, another one of $Z_1'$, $Z_2'$, $Z_3'$ and $Z_4'$ represents Z, and the remainder of $Z_1'$, $Z_2'$, $Z_3'$ and $Z_4'$ represents a hydrogen atom and/or a protective group, one of R and Z represents $A_1$ and the other represents $A_2$, $A_1$ being an acyl group having 14 to 22 carbon atoms which does not contain a carboxyl group and $A_2$ being an acyl group having 2 to 14 carbon atoms and having one carboxyl group, X represents a hydrogen atom or a halogen atom (compound Ia); a 2,2'-anhydro product of Compound Ia wherein $Z_2'$ represents a hydrogen atom (Compound Ib); an arabinosylation product of Compound Ia (Compound Ic); a deamination product of Compound Ia (Compound Id); a 2'-deoxy product of Compound Id wherein $Z_2'$ represents a hydrogen atom (Compound Ie); a salt of Compound Ia, Ib, Ic, or Id or Ie having an $A_2$ group with a base (Compound If); and a salt of Compound Ia, Ib or Ic, wherein $Z_1'$ represents a hydrogen atom, with an acid (Compound Ih); and processes for preparing the same.

The present invention provides compounds represented by formula (I) above which are water-soluble and useful as antileukemia, e.g., in mice, agents having a stable antileukemial activity in a living body, e.g., in mice, or which are useful as intermediates for the preparation of such antileukemia, e.g., in mice, agents.

DETAILED DESCRIPTION OF THE INVENTION

The process of this invention comprises reacting a compound selected from the compounds represented by formula (II):

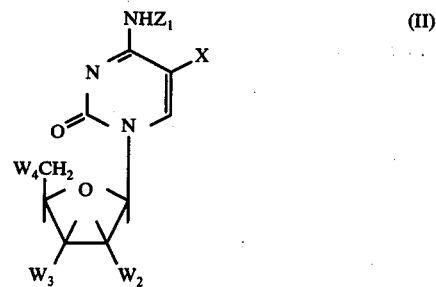

wherein one of $Z_1$, $W_2$, $W_3$ and $W_4$ can be an activated functional group; when $Z_1$ represents an activated functional group, $W_2$, $W_3$ and $W_4$ represent $OZ_2$, $OZ_3$ and $OZ_4$, respectively, and one of $Z_2$, $Z_3$ and $Z_4$ represents R as earlier defined and the remainder of $Z_2$, $Z_3$ and $Z_4$ represents a hydrogen atom and/or a protective group; when $W_2$ represents an activated functional group, $W_3$ and $W_4$ represent $OZ_3$ and $OZ_4$, respectively, and one of $Z_1$, $Z_3$ and $Z_4$ represents R and the remainder of $Z_1$, $Z_3$ and $Z_4$ represents a hydrogen atom and/or a protective group; when $W_3$ represents an activated functional group, $W_2$ and $W_4$ represent $OZ_2$ and $OZ_4$, respectively, and one of $Z_1$, $Z_2$ and $Z_4$ represents R as earlier defined and the remainder of $Z_1$, $Z_2$ and $Z_4$ represents a hydrogen atom and/or a protective group; when $W_4$ represents an activated functional group, $W_2$ and $W_3$ represent $OZ_2$ and $OZ_3$, respectively, and one of $Z_1$, $Z_2$ and $Z_4$ represents R and the remainder of $Z_1$, $Z_2$ and $Z_4$ represents a hydrogen atom and/or a protective group; when any one of $Z_1$, $W_2$, $W_3$ and $W_4$ does not represent an activated functional group, $W_2$, $W_3$ and $W_4$ represent $OZ_2$, $OZ_3$ and $OZ_4$, respectively, and one of $Z_1$, $Z_2$, $Z_3$ and $Z_4$ represents a hydrogen atom and another one of $Z_1$, $Z_2$, $Z_3$ and $Z_4$ represents R and the remainder of $Z_1$, $Z_2$, $Z_3$ and $Z_4$ represents a hydrogen atom and/or a protective group; R represents $A_1$ or $A_2$, $A_1$ being an acyl group having 14 to 22 carbon atoms which does not contain a carboxyl group and $A_2$ being an acyl group having 2 to 14 carbon atoms and having one carboxyl group; X represents a hydrogen atom or a halogen atom such as fluorine, chlorine, bromine or iodine (Compound IIa); a 2,2'-anhydro product of compound IIa wherein $W_2$ represents a hydroxyl group (Compound IIb); an arabinosylation product of Compound IIa (Compound IIc); a deamination product of Compound IIa (Compound IId); a 2'-deoxy product of Compound IId (Compound IIe); a salt of Compound IIa, IIb, IIc or IId or IIe having an $A_2$ group with a base (Compound IIf); and a salt of Compound IIa, IIb or IIc wherein $Z_1$ represents a hydrogen atom with an acid (Compound IIh), with an acylating agent represented by the formula

ZW wherein Z represents an $A_2$ group when Compound II has an $A_1$ group, or Z represents an $A_1$ group when Compound II is a deamination product of Compound IIa wherein $Z_1$ represents R, or a 2'-deoxy product of the deamination product, wherein $A_1$ and $A_2$ are as defined above, the above acylating agent being selected from the group consisting of acids, acid salts, acyl halides acylazides, acid anhydrides, amides and esters thereof in a proportion of 1.0 to 1.3 or 1.0 to 100 mols of the acylating agent per mol of Compound II in a solvent selected from basic solvents, neutral solvents free of any hydroxyl group, neutral solvent containing one or more hydroxyl groups and acidic solvents in an amount of 10 to 100 times the total weight of Compound II and the acylating agent, at a pressure of 1 to 2 atms, either at a temperature of about 0° to about 30° C for a period of about 5 minutes to 3 hours in the case when Compound II has an activated functional group or when a condensing agent and/or a basic solvent is used in the reaction, or at a temperature of about 20° to about 80° C for a period of about 2 to about 20 hours in remaining cases, to produce a compound represented by the formula I (Compound I):

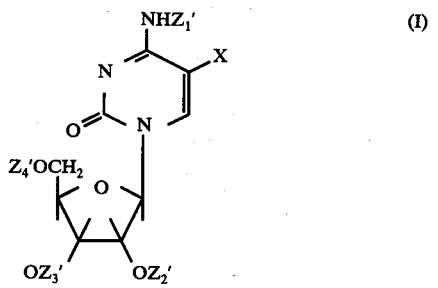

wherein X is as defined above, and one of $Z_1'$, $Z_2'$, $Z_3'$ and $Z_4'$ represents R which is defined above, another one of $Z_1'$, $Z_2'$, $Z_3'$ and $Z_4'$ represents Z which is defined above and the remainder of $Z_1'$, $Z_2'$, $Z_3'$ and $Z_4'$ represents a hydrogen atom and/or a protective group, and where Z corresponds to Z of the acylating agent having the formula ZW (Compound Ia); a 2,2'-anhydro product of Compound Ia wherein $Z_2'$ represents a hydrogen atom (Compound Ib); an arabinosylation product of Compound Ia (Compound Ic); a deamination product of Compound Ia (Compound Id); a 2'-deoxy product of Compound Id wherein $Z_2'$ represents a hydrogen atom (Compound Ie); a salt of Compound Ia, Ib, Ic, or Id or Ie having an $A_2$ group with a base (Compound If); and a salt of Compound Ia, Ib or Ic wherein $Z_1'$ represents a hydrogen atom with an acid (Compound Ih).

Compounds Ia and Ic of the present invention are represented by the formula (I')

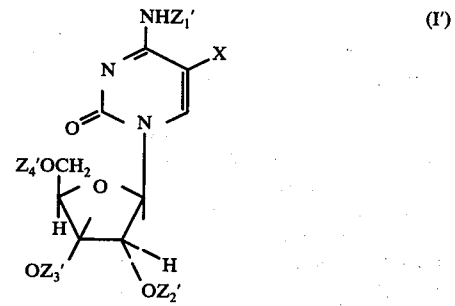

wherein $Z_1'$, $Z_2'$, $Z_3'$, $Z_4'$ and X are as defined above.

In the above reaction, the type and amount of acylating agent comprising a Z moiety and the type of solvent used vary depending upon the presence or absence of an activated functional group in Compound II to be acylated, i.e., Reaction (1) in which one of $Z_1$, $W_2$, $W_3$ and $W_4$ of Compound II represents an activated functional group and Reaction (2) in which neither $Z_1$, $W_2$, $W_3$ nor $W_4$ of Compound II represents an activated functional group.

In Reaction (1), an acylating agent selected from those derived from acids or salts in an amount of 1.0 to 100 mols per mol of the compound of formula II and a solvent selected from basic solvents and neutral solvents free of a hydroxyl group can be used.

In Reaction (2), the type and the amount of acylating agent and the type of solvent which can be used further vary depending upon the type of Compound II to be acylated, i.e., Reaction (2A) where one of $Z_1$, $Z_2$, $Z_3$ and $Z_4$ represents a hydrogen atom and Reaction (2B) where two or three of $Z_1$, $Z_2$, $Z_3$ and $Z_4$ represents hydrogen atoms. However, in both Reactions (2A) and (2B), when an acylating agent selected from those derived from acids and salts is used, a condensing agent is used in combination with the acylating agent in an amount of 1.0 to 100 mols of the condensing agent per mol of Compound II.

In Reaction (2A), an acylating agent is selected from those derived from acids, salts, acyl halides, acyl azides, acid anhydrides, amides and esters in an amount of 1.0 to 100 mols per mol of the Compound II. In Reaction (2A), a basic solvent is used in combination with an acylating agent selected from acid salts, acyl halides, acyl azides, acid anhydrides, amides or esters for acylating the $N^4$-, 2'-, 3'- or 5'-position.

In Reaction (2A) a neutral solvent free of a hydroxyl group is used in combination with an acylating agent selected from acids, salts thereof, acyl azides, acid anhydrides, amides or esters for acylating the $N^4$-, 2'-, 3'- or 5'-positon, and such a solvent can also be used in combination with an acid halide acylating agent for acylating the 2'-, 3'- or 5'-position.

In Reaction (2A) a neutral solvent containing one or more hydroxyl groups is used in combination with an acid anhydride acylating agent for acylating $N^4$-position.

In Reaction (2B), the type and the amount of acylating agent and the type of solvent vary depending upon the position of Compound II to be acylated.

In Reaction (2B), in acylating the $N^4$-position, the combination of an acid halide acylating agent in an amount of 1.0 to 100 mols per mol of Compound II and a neutral solvent containing one or more hydroxyl groups is used or, alternatively, a combination of an acylating agent selected from the acyl azides, acid anhydrides, amides and esters in an amount of 1.0 to 1.3 mol per mol of Compound II and a solvent selected from basic solvents and neutral solvents free of a hydroxyl group can be used.

In acylating the 5'-position of Compound II, or the 2' or 3'-position of Compound II wherein $W_4$ represents the R group or a protective group, a combination of an acylating agent selected from acids, salts, acyl halides, acyl azides, acid anhydrides, amines and esters in an amount of 1.0 to 1.3 mol per mol of Compound II and either (1) a basic solvent in the case of Compound IIa, IIb and IIc and a salt of Compound IIa, IIb and IIc with a base wherein $Z_1$ represents the R group or a protective group and in the case of Compound IId and IIe and a salt of Compound IId and IIe with a base; (2) a neutral solvent free of a hydroxy group in the case described above for the Compounds as in (1) and additionally in the case of Compound IIh; or (3) an acidic solvent in the case where the $N^4$-position of Compound II is free.

In acylating the 3'-position of Compound II wherein the 5'-position is substituted with a hydroxyl group, a combination of an α-acyloxyacyl halide as an acylating agent and a basic solvent is used.

In acylating the 2'-position of Compound II wherein the 5'-position is substituted with a hydroxyl group, Compound II is first protected with a protective group such as a triphenylmethyl group and then acylated as described previously.

Compound I and Compound II as well as the acylating agent (ZW) and the solvent(s) used in the acylation of Compound II to produce Compound I are hereinafter described in great detail.

Representative examples of acyl groups having 14 to 22 carbon atoms but free of any carboxylic acid group, i.e. $A_1$, which can be present in Compound I, Compound II or the acylating agent ZW are aliphatic acyl groups such as myristoyl, palmitoyl, margaroyl, stearoyl, n-nonadecanoyl, arachidoyl, n-heneicosanoyl, behenoyl, oleoyl, arachidonoyl, and aliphatic acyl groups substituted with halogen such as fluorine, chlorine, bromine and iodine; hydroxyl; mercapto; phenyl; phenoxyl; thiophenoxyl; nitrophenyl; cycloalkyl having 4 – 7 carbon atoms such as cyclohexyl; heterocyclic groups having 1 – 6 carbon atoms such as 2-thienyl, 2-tetrahydropyranyloxy; alkyloxy having 1–4 carbon atoms such as methoxy; thioalkyloxy having 1 – 4 carbon atoms such as thiomethoxy; carboxyalkyl having 2 – 5 carbon atoms such as carboxymethyl; epoxy; and oxo, such as 2-chlorostearoyl, 18-hydroxystearoyl, 2-mercaptostearoyl, phenyllauroyl, phenoxylauroyl, p-nitrophenyllauroyl, thiophenoxylauroyl, cyclohexyllauroyl, 14-(2-thienyl)myristoyl, 14-(2-tetrahydropyranyloxy)myristoyl, 18-methoxystearoyl, 18-thiomethoxystearoyl, 16-carboxymethylpalmitoyl, 12,13-epoxy-9-octadecanoyl, 4-oxostearoyl and the like, preferably palmitoyl, stearoyl, nonadecanoyl, arachiodoyl, heneicosanoyl and behenoyl, most preferably stearoyl, nonadecanoyl, arachidoyl, heneisonoyl and behenoyl.

Representative examples of acyl groups having 2 to 14 carbon atoms and which have one carboxylic acid group, i.e. $A_2$, which can be contained in Compound I, Compound II or the acylating agent ZW are acyl groups having no substituent groups except one carboxyl group, acyl groups having substituent groups such as phenyl, hydroxyl, halogen such as fluorine, chlorine, bromine, iodine; N-carbobenzyloxyamino, cycloalkyl having 4 – 7 carbon atoms such as cyclohexyl, mercapto, nitro, hetrocyclic groups having 1 – 6 carbon atoms such as furane, pyridine; oxo, adamantane, carboxylic acids, oxyalkylcarboxylic acids having 2 – 4 carbon atoms such as oxymethenylcarboxylic acid, thioalkyl carboxylic acids having 2 – 4 carbon atoms such as thiomethenylcarboxylic acid; such as hemifumaroyl, 4-carboxymethylphenylacetyl, hemitartroyl, hemiterephthaloyl, hemisuccinyl, hemicitraconyl, hemihomophthaloyl, hemibromosuccinyl, hemi-N-carbobenzyloxy-L-aspartyl, 1'-carboxymethylcyclohexylacetyl, hemidiglycoloyl, hemihydroxytartroyl, hemiitaconyl, hemiglutaryl, hemimercaptosuccinyl, hemimucoyl, heminitrosuccinyl, 1-carboxycyclobutanecarbonyl, 4-carboxyfurane-3-carbonyl, 5-carboxypyridine-2-carbonyl, 3-carboxyacetonecarbonyl, 3-carboxymethyladamantaneacetyl, hemichloromaleoyl, hemidithioglycoloyl and the like, preferably hemisuccinyl.

Representative examples of protective groups which can be present in Compound I or Compound II are alkylidene groups having 2 – 4 carbon atoms such as isopropylidene, ethylidene; benzylidene; cyclic or acyclic acetal groups such as tetrahydropyranyl, tetrahydrofuranyl, ethoxyethyl, methoxymethyl, ethoxymethyl, methoxyethyl; triphenylmethyl; 2,4-dinitroanilino; (alkyl having 1 – 4 carbon atoms) oxycarbonyl such as methoxycarbonyl; tri(halo)(alkyl having 1 – 4 carbon atoms)oxycarbonyl groups such as trichloroethoxycarbonyl, tribromoethoxycarbonyl; formyl; trihaloacetyl groups such as trifluoroacetyl, trichloroacetyl; benzyl; benzhydrine, 2,4-dinitrophenylsulphenyl; propenyl; borate; vinylthioether; and benzoylpropyl.

Representative examples of an actived functional group which can be present in Compound II are a trimethylsilyl group at the $N^4$-position, chlorine, bromine and iodine, a methansulfonyloxy or a p-nitrotoluenesulfonyloxy group at the 2', 3' or 5'-position, and the like.

Representative examples of Compounds If and Ih and Compounds IIf and IIh are alkali metal salts such as sodium salts, potassium salts, alkali earth metal salts such as calcium salts; ammonium salts; organic amine salts such as trimethylamine salts, triethylamine salts, procaine salts, dibenzylamine salts, N-benzyl-β-phenylamine salts, N,N'-dibenzylethylenediamine salts and choline salts of Compounds Ia, Ib, Ic, Id and Ie and Compounds IIa, IIb, IIc, IId and IIe; and mineral acid salts such as hydrochloric acid salts and sulfuric acid salts; and carboxylic acid salts having 1 to 4 carbon atoms such as formic acid salts of Compounds Ia, Ib and Ic and Compounds IIa, IIb and IIc wherein $Z_1$ represents a hydrogen atom; and the like.

Of these salts of Compounds If, Ih, IIf and IIh, sodium salts, potassium salts, calcium salts, ammonium salts, trimethylamine salts, triethylamine salts, procaine salts, dibenzylamine salts, N-benzyl-β-phenethylamine salts, N,N'-dibenzylethylenediamine salts preferred in view of their excellent water solubility. Further, variations in the $A_1$ group affect the pharmacological activity to a greater degree than variations in the $A_2$ group.

Representative examples of acids are monocarboxylic acids having 14 – 22 carbon atoms such as aliphatic acids and aliphatic acids substituted with halogen such as fluorine, chlorine, bromine and iodine; hydroxyl;

mercapto; phenyl; phenoxy; thiophenoxy; nitrophenyl; cycloalkyl having 4 – 7 carbon atoms such as cyclohexyl; hetrocyclic groups having 1 – 6 carbon atoms such as 2-thienyl, 2-tetrahydropyranyloxy; alkyloxy having 1 – 4 carbon atoms such as methoxy; thioalkyloxy having 1 – 4 carbon atoms such as thiomethoxy; caboxyalkyl having 2 – 5 carbon atoms such as carboxymethyl; epoxy; and oxo; such as myristic acid, palmitic acid, margaric acid, stearic acid, n-nonadecanoic acid, arachidic acid, n-heneicosanoic acid, behenic acid, oleic acid, arachidonic acid, 2-chlorostearic acid, 18-hydroxystearic acid, 2-mercaptostearic acid, phenyllauric acid, phenoxylauric acid, p-nitrophenyllauric acid, thiophenoxylauric acid, cyclohexyllauric acid, 14-(2-thienyl)myristic acid, 14-(2-tetrahydropyranyloxy)myristic acid, 18-methoxystearic acid, 18-thiomethoxystearic acid, 16-carboxymethylpalmitic acid, 12,13-epoxy-9-octadecanoic acid, 4-oxostearic acid, and dicarboxylic acids having 2 – 12 carbon atoms such as acids having no substituent groups; acids having substituent groups such as phenyl, hydroxyl, halogen such as of fluorine, chlorine, bromine, iodine; N-carbobenzyloxyamino, cycloalkyl having 4 – 7 carbon atoms such as cyclohexyl, mercapto, nitro, heterocyclic groups having 1 – 6 carbon atoms such as furan, pyridine; oxo, adamantane; and acids having hetero atoms such as oxygen or sulfur in the carbon chain; such as fumaric acid, p-phenylenediacetic acid, tartaric acid, terephthalic acid, succinic acid, citraconic acid, homophthalic acid, bromosuccinic acid, L-N-carbobenzyloxyaspartic acid, 1,1-cyclohexanediacetic acid, diglycolic acid, dihydroxytartaric acid, itaconic acid, glutaric acid, mercaptosuccinic acid, mucic acid, nitrosuccinic acid, 1,1-cyclobutanedicarboxylic acid, 3,4-furandicarboxylic acid, 2,5-pyridine-dicarboxylic acid, 13-acetonedicarboxylic acid, 1,3-adamantanediacetic acid, chloromaleic acid, dithioglycolic acid and the like.

Representative examples of salts as an acylating agent are alkali metal salts, alkaline earth metal salts, ammonium salts and organic base salts of the above acids such as, for example, lithium 18-hydroxystearate, sodium 2-mercaptostearate, potassium fumarate, magnesium tartrate, calcium dihydroxytartrate, diammonium terephthalate, trimethylaminemercaptosuccinate, tetra(trimethyl)amine mucate and the like.

Representative examples of acyl halides such as acyl chlorides, acyl bromides, etc., as an acylating agent are chlorides or bromides of the representative acyl groups for Z, such as myristoyl chloride, cyclohexyllauroyl bromide, fumaroyl chloride, itaconyl chloride and the like.

Representative examples of acyl azides as an acylating agent are azides of the representative acyl groups for Z, such as terephthaloyl azide, phenyllauroyl azide and the like.

Representative examples of acid anhydrides as an acylating agent are anhydrides of homo acids such as myristic anhydride, palmitic anhydride, margaric anhydride, n-nonadecanoic anhydride, arachidic anhydride, n-heneicosanoic anhydride, behenic anhydride, oleic anhydride, arachidonic anhydride, 2-chlorostearic anhydride, phenyllauric anhydride, phenoxylauric anhydride, p-nitrophenyllauric anhydride, thiophenoxylauric anhydride, cyclohexyllauric anhydride, succinic anhydride, diglycolic anhydride, glutaric anhydride, nitrosuccinic anhydride, dithioglycolic anhydride and the like, and anhydrides of mixed acids such as 14-(2-thienyl)myristic formic anhydride, terephthalic benzoic anhydride, stearic ethylphosphoric anhydride, behenic benzylphosphoric anhydride, fumaric dimethylphosphite anhydride, myristic benzenesulfonic anhydride and the like.

Representative examples of amides as an acylating agent are 1-imidazole derivatives of the representative acyl groups for Z such as 1-phenyllauroylimidazole, 1-phenoxylauroyl, 1-(4-carboxymethylphenyl)acetylimidazole, 1-citraconoylimidazole and the like.

Representative examples of esters as an acylating agent are those formed from the above representative acids and alcohols such as cyanoethyl palmitate, p-nitrophenyl margarate, propargyl arachidate, biphenyl oleate, methoxymethyl 3,4-furandicarbonate, pyranyl chloromaleyl, N-stearate succinimide and the like.

Representative examples of condensing agents which can be used in combination with acids or salts as acylating agent are N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(13-dimethylaminopropyl)carbodiimide, N,N'-carbonyl-di-(2-methylimidazole), N-cyclohexylimine, diphenylketone-N-cyclohexylamine and the like.

The solvents which can be used in the reaction of the present invention can be classified into netural solvents, basic solvents and acidic solvents in nature. Further, the neutral solvents can be classified into those containing one or more hydroxyl groups and those free of any hydroxyl group.

Representative examples of neutral solvents free of any hydroxyl groups are dioxane, acetone, acetonitrile, N,N-dimethylacetamide (DMA), N,N-dimethylformamide (DMF), dimethylsulfoxide (DMSO), tetramethylurea, hexamethyl phosphoramide, tetramethylenesulfone, propylene carbonate, nitrobenzene, nitromethane, dimethyl cyanamide, tetrahydrofuran (THF), chloroform and the like.

Representative examples of neutral solvents which contain one or more hydroxyl groups are methanol and ethanol; and dioxane, DMA, DMF, DMSO and THF which contain water, methanol or ethanol in a 1 to 100 molar amount, based on the amount of the acylating agent.

Representative examples of basic solvents are pyridine; and dioxane, DMA, DMF, DMSO and THF which contain potassium bicarbonate, sodium bicarbonate, trimethylamine, triethylamine or pyridine in a 1 to 100 molar amount based on the amount of the acylating agent used, and the like.

Representative examples of acidic solvents are dioxane, DMA, DMF, DMSO and THF which contain hydrochloric acid or sulfuric acid in an equimolar amount relative to Compound II.

A preferred embodiment for isolating the desired product, Compound I, from the reaction mixture upon completion of the reaction is described hereinbelow in detail. Unless otherwise indicated, all procedures were conducted at atmospheric pressure and at room temperature (about 20°–25° C).

After completion of the reaction, any insoluble materials are removed by filtration when a basic solvent is used, and the solvent is evaporated from the reaction mixture at a pressure of about 0.1 to about 0.5 atm. at a temperature of about 40° to about 60° C. When an acid halide and a neutral solvent are used, sodium bicarbonate in an equimolar amount to the acid halide is added to the reaction mixture at a temperature of about 5° C to render the reaction mixture neutral and thereafter the solvent is evaporated in the same manner as described above. In other cases, ice water is added to the reaction mixture in a 10 to 100 molar amount relative to the acylating agent used and thereafter the solvent is evaporated. The resulting residue is cooled to about 5° C, and water cooled to about 5° C is added to the residue in an amount of 10 to 100 times the amount (by weight) of the residue. The mixture is then stirred at about 5° C for a period of about 10 minutes and filtered. The addition of water followed by filtration as described above is repeated 2 to 5 times to wash the reaction mixture and then the reaction mixture is air dried. The solid thus obtained is then heated in benzene, toluene, ethyl acetate, etc., in an amount of 10 to 100 times the weight of the solid while refluxing for 1 to 4 hours. The mixture is then allowed to cool to room temperature and filtered. The heating in benzene and the like followed by filtration as described above is repeated three times to wash the reaction mixture, and the resulting solid is air-dried. Tetrahydrofuran is then added to the solid in an amount of 5 to 20 times the weight of the solid, and the mixture is heated at a temperature of about 80° C to dissolve the solid. Water is then added, if necessary, in an amount equal to the tetrahydrofuran and the mixture is allowed to cool to room temperature to obtain a white precipitate of Compound I. The white precipitate thus obtained is then filtered and air-dried to obtain desired Compound I. Compound I thus obtained can be identified by ultraviolet absorption spectral analysis and infrared absorption spectral analysis.

As previously set forth, Compound I includes Compound Ia (cytidine derivatives), Compound Ib (2,2-anhydrocytidine derivatives), Compound Ic (cytosine arabinoside derivatives), Compound Id (uridine derivatives), Compound Ie (2′-deoxyuridine derivatives), Compound If (salts of Compound Ia, Ib, Ic, or Id or Ie having an $A_2$ group with a base) and Compound Ih (salts of Compound Ia, Ib or Ic wherein $Z_1$ represents a hydrogen atom with an acid). Compound Ia can be converted into the Compound Ib, and Compound Ib can be converted into the Compound Ic. Compound Id or Ie where the 5-position is not halogenated can be converted into Compound Id or Ie wherein the 5-position is brominated. Compound Ih can be converted into Compound Ia, Ib or Ic, and Compound Ia, Ib or Ic, or Compound Id or Ie having an $A_2$ group can be converted into Compound If.

The above conversions between the Compounds I are hereinafter described in detail. Unless otherwise indicated, all procedures were conducted at atmospheric pressure and at room temperature (about 20°–25° C).

The conversion of Compound Ia to Compound Ic via Compound Ib differs depending upon the type of $Z_2'$ group in Compound Ia, i.e., a hydrogen atom, a protective group or an acyl group.

When the group $Z_2'$ in Compound Ia is a hydrogen atom, an equimolar amount of phosphorus oxychloride and an equimolar amount of t-butyl alcohol relative to Compound Ia are added to Compound Ia followed by stirring for 1 to 2 hours. The resulting reaction mixture is then concentrated at 0.1 to 0.5 atm. at a temperature of about 40° to 60° C. The residue thus obtained is then dissolved in tetrahydrofuran in an amount of about 10 to 100 times the weight of the residue and water in an amount equal to the weight of tetrahydrofuran is added to the solution. The white precipitate formed is collected by filtration and air-dried to obtain Compound Ib as a white powder. Compound Ib is then added to a 2% ethanolic sodium bicarbonate solution in an amount of about 100 times the weight of Compound Ib and the mixture is stirred for about 1 to 20 hours. The reacton mixture is filtered, and the filtrate concentrated at 0.1 to 0.5 atm. at a temperature of about 40° to 50° C. The residue thus obtained is then re-precipitated from a mixture of tetrahydrofuran and water as described above to obtain the desired Compound Ic.

When the group $Z_2'$ in Compound Ia is a protective group, Compound Ia can be converted into Compound Ic via Compound Ib as described above after cleaving the protective group as described hereinafter.

When the group $Z_2'$ in Compound Ia is an acyl group, tetrahydrofuran in an amount of about 100 times the weight of Compound Ia and absolute methanol in an amount of about 100 times the weight of Compound Ia are added to Compound Ia to dissolve Compound Ia. To the solution is added 2.5N sodium methoxide in an amount of about 15 times the weight of Compound Ia followed by stirring for about 5 to 10 minutes. To the resulting reaction mixture is added Dowex-50 (ion-exchange resin; pyridine salt form) in an amount corresponding to a 1 to 10 molar amount relative to the sodium methoxide, followed by stirring for about 10 minutes. Then, the Dowex-50 is filtered off, and the filtrate is concentrated at 0.1 to 1.5 atm. at a temperature of about 40° to 60° C. This procedure results in the cleavage of the acyl group at the 2′-position of Compound Ia and the compound thus obtained free of an acyl group at the 2′-position can then be subjected to the arabinosylation previously described. The arabinosyl derivative obtained can be re-acylated in accordance with the process of this invention to obtain Compound Ic.

Compound Id or Ie in which the 5-position is not halogenated can be brominated at 5-position as follows. Dioxane is added to Compound Id or Ie in an amount of 10 to 100 times the weight of Compound Id or Ie to dissolve the compound. The resulting solution is cooled to about 5° C, and a solution of bromine in chloroform (10% solution) containing an equimolar amount of bromine relative to Compound Id or Ie is added dropwise to Compound Id or Ie while stirring at a temperature of about 5° C. After completion of the addition, the stirring is further continued for an additional one hour at about 5° C. Upon completion of the reaction, pyridine is added in an amount equimolar to the bromine used at a temperature of 5° C to neutralize the hydrogen bromide formed during the reaction. The reaction mixture is concentrated at 0.1 to 0.5 atm. at a temperature of about 40° to 60° C, and tetrahydrofuran is added to the residue in an amount of about 10 to 100 times the weight of the residue followed by heating at a temperature of about 60° C to dissolve the residue. The resulting solution is cooled to about 5° C, and water is added to the solution in an amount equal to the tetrahydrofuran used. The precipitate formed is collected by filtration and air-dried to obtain Compound Id or Ie in which the 5-position is brominated.

Compound Ih can be converted into Compound Ia, Ib or Ic as follows. Pyridine is added to Compound Ih in a 1 to 10 molar amount relative to the amount of Compound Ih, and the resulting solution is concentrated at 0.1 to 0.5 atm. at a temperature of about 40° to 60° C. To the resulting residue is added tetrahydrofuran in an amount of about 10 to 100 times the weight of the residue followed by heating at about 60° C to dissolve the residue. Water is then added to the solution in an amount equal to the weight of the tetrahydrofuran, and the mixture is cooled to about 5° C. The white precipitate formed is collected by filtration and air-dried to obtain the desired Compound Ia, Ib or Ic.

Compound Ia, Ib or Ic, or Compound Id or Ie containing an $A_2$ group can be converted into Compound If by the following procedure. Compound Ia, Ib, Ic, Id or Ie is dissolved in tetrahydrofuran in an amount of 10 to 100 times (by weight) the compound at a temperature of about 80° C. The solution is then allowed to cool to room temperature, and an equimolar amount (relative to Compound Ia, Ib, Ic, Id or Ie) of a bicarbonate or carbonate salt such as sodium bicarbonate, potassium bicarbonate, ammonium bicarbonate, trimethylammonium bicarbonate, triethylammonium bicarbonate, procaine carbonate, dibenzylammonium bicarbonate, N-benzyl-$\beta$-phenethyl ammonium bicarbonate, or choline carbonate or a 0.5 molar amount of calcium carbonate or N,N'-dibenzylethylenediammonium bicarbonate is added to the solution followed by stirring the solution until the bicarbonate or carbonate salt dissolves (30 minutes to 4 hours). After completion of the reaction, the reaction mixture is filtered, and the filtrate is concentrated at 0.1 to 1.5 atm. at a temperature of about 40° to 50° C. The resulting residue is freeze-dried in vacuo at a temperature of $-40°$ C to obtain the desired Compound If.

When Compound I contains a protective group(s), these protective group(s) can be cleaved according to the well-known technique commonly employed for removing protective groups. A typical procedure for cleaving the protective group is illustrated below in which all procedures were conducted at atmospheric pressure and at room temperature (about 20° to 25° C) unless otherwise indicated.

Compound I containing a trichloroethoxycarbonyl group as a protective group is reacted with zinc powder in an amount of about 5 mols per mol of Compound I in 80% acetic acid in an amount of about 5 to 50 times the total weight of Compound I and zinc powder for a period of about 20 hours. The zinc powder is then removed by filtration and the filtrate concentrated in vacuo at a temperature of about 40° to 60° C. The resulting residue is added to tetrahydrofuran in an amount of about 10 times the weight of the residue followed by heating at 80° C to dissolve the residue. The solution is cooled to room temperature, and an equivalent amount of water added to the solution. The white precipitate formed is separated by filtration to obtain the desired Compound I from which the trichloroethoxycarbonyl protective group has been removed.

When the protective group is a triphenylmethyl group, trifluoroacetic acid is reacted with Compound I having the above protective group in a 5 molar amount relative to compound I in tetrahydrofuran in an amount of 5 to 50 times the total weight of Compound I and trifluoroacetic acid for a period of about 4 hours, and the reaction mixture is then concentrated at 0.1 to 0.5 atm. at a temperature of about 40° to 60° C. The resulting residue is re-precipitated from tetrahydrofuran as described above to obtain the desired Compound I from which the triphenylmethyl protective group has been removed.

When the protective group is a tetrahydropyranyl group, Compound I having this protective group is reacted with hydrochloric acid in an amount of about 0.1 mol relative to Compound I in tetrahydrofuran in an amount of 5 to 50 times the total amount of Compound I and the hydrochloric acid at a temperature of about 80° C for about 20 hours. The reaction mixture is concentrated at 0.1 to 0.5 atm. at a temperature of about 40° to 60° C, and the resulting residue re-precipitated from tetrahydrofuran as described above to obtain the desired Compound I from which the tetrahydropyranyl protective group has been removed.

When the protective group is a benzyl group, Compound I having this protective group is contacted with hydrogen gas in the presence of palladium in a 0.1 molar amount based on the amount of Compound I in tetrahydrofuran in an amount of about 5 to 50 times the total weight of Compound I and the palladium for about 4 hours. The palladium is removed by filtration, and the filtrate is concentrated at 0.1 to 0.5 atm. at a temperature of about 40° to 60° C. The resulting residue is then re-precipitated from tetrahydrofuran as described above to obtain the desired Compound I from which the benzyl protective group has been removed.

Of Compound I having no protecting group thus obtained, a salt of Compound Ic and a base is soluble in water and is markedly effective for improving the survival ratio in L-1210 leukemia mice. Also, Compounds Ia and Ib are useful as intermediates for the synthesis of Compound Ic. The 5-halogenated forms of Compounds Id and Ie are also markedly effective for improving the survival ratio of L-1210 leukemia mice. Compounds Id and Ie wherein the 5-position is not halogenated are also useful as intermediates for the synthesis of the 5-halogenated form of Compounds Id and Ie.

Compound II, or the starting materials for preparing Compound II, i.e., a nucleoside such as cytidine, 5-halocytidine, 2,2'-anhydrocytidine, 2,2'-anhydro-5-halocytidine, cytosine arabinoside, 5-halocytosine arabinoside, uridine, 5-halouridine, 2'-deoxyuridine and 2'-deoxy-5-halouridine are, as described previously, commercially available or can easily be prepared by one skilled in the art.

Compound II can be prepared according to the technique described in the references given previously by acylating the nucleoside thereof or, if necessary, introducing protective groups prior to or after the acylation, or introducing reactive groups after the acylation. A typical embodiment of the preparation of Compound II is illustrated below in which all procedures were conducted at atmospheric pressure and at room temperature (about 20° to 25° C) unless otherwise indicated.

An $N^4$-acylnucleoside can be obtained by reacting a nucleoside with a 2 molar amount of an acid anhydride as an acylating agent in a solvent mixture of water and dioxane in an amount of about 10 to 100 times the total weight of the nucleoside and the acid anhydride at a temperature of about 80° C for a period of about 4 hours.

A 5'-O-acylnucleoside can be obtained by reacting a hydrochloride salt of the nucleoside with an acid anhydride or an acid halide as an acylating agent in an amount of about 1.1 mols of the acylating agent per mol of the hydrochloride salt in dimethylacetamide in an amount of about 10 to 100 times the total weight of the nucleoside hydrochloride and the acylating agent at room temperature for 20 hours.

A 2'- or 3'-O-acylnucleoside can be prepared by reacting a hydrochloride salt of a 5'-O-tritylnucleoside with an acid anhydride as an acylating agent in an amount of about 1.2 mols of the acylating agent per mol of the hydrochloride salt in dimethylacetamide in an amount of about 10 to 100 times the total weight of the nucleoside hydrochloride and the acylating agent at room temperature for 20 hours, subjecting the reaction product to silica gel chromatography to separate a fraction containing the desired 2'- or 3'-O-acyl-5'-tritylnucleoside, and cleaving the trityl group from the resulting acylate.

An $N^4$-trihaloethoxycarbonyl nucleoside can be obtained by reacting a nucleoside with a trihaloethoxycarbonyl halide in an amount of 1.2 mols of the halide per mol of the nucleoside in pyridine in an amount of about 10 to 100 times the total weight of the halide and the nucleoside at a temperature of 5° C for 20 hours. Conversely, the $N^4$-trihaloethoxycarbonyl nucleoside can be reacted with zinc power in an amount of about 5 mols per mol of the nucleoside in 80% acetic acid in an amount of about 10 to 100 times the total weight of the zinc powder and the nucleoside at room temperature for 20 hours to obtain the nucleoside from which the trihaloethoxycarbonyl group has been removed.

An acid addition salt of a nucleoside can be obtained by reacting the nucleoside with an inorganic acid in an amount of 1.0 mol per mol of the nucleoside in dimethylacetamide in an amount of 10 to 100 times the total weight of the nucleoside and the inorganic acid at a temperature of 5° C for about 5 hours. Conversely, the acid addition salt of a nucleoside can be reacted with pyridine in an amount of about 2 mols per mol of the salt at room temperature for about 5 hours to obtain a free nucleoside.

A 5'-O-trityl nucleoside can be obtained by reacting a nucleoside with a triphenylmethyl halide in an amount of 1.1 mols per mol of the nucleoside in pyridine in an amount of about 10 to 100 times the total weight of the nucleoside and the halide at room temperature for 20 hours. Conversely, the 5'-O-trityl nucleoside can be reacted with trifluoroacetic acid in an amount of 5 mols per mol of the nucleoside in chloroform in an amount of about 10 to 100 times the total weight of the nucleoside and the trifluoroacetic acid at room temperature for 4 hours to obtain a free nucleoside.

A 2'-, 3'- or 5'-O-tetrahydropyranyl nucleoside can be obtained by reacting a nucleoside with 0.1 mol of an inorganic acid and 10 mols of dihydropyrane per mol of the nucleoside at a temperature of 80° C for about 2 hours. Conversely, the 2'-, 3'- or 5'-O-tetrahydropyranyl nucleoside can be reacted with an inorganic acid in an amount of 0.1 mol per mol of the nucleoside in dimethylacetamide in an amount of about 10 to 100 times the total amount of the nucleoside and the inorganic acid at a temperature of about 80° C for about 2 hours to obtain the nucleoside.

A 2'-, 3'- or 5'-O-benzyl nucleoside can be obtained by reacting a nucleoside with a benzyl halide in an amount of 1.2 mols per mol of the nucleoside in pyridine in an amount of about 10 to 100 times the total amount of the nucleoside and the benzyl halide at room temperature for about 20 hours. Conversely, the 2'-, 3'- or 5'-O-benzyl nucleoside can be reacted with hydrogen gas in the presence of a palladium catalyst in an amount of 0.1 mol of the catalyst per mol of the nucleoside in N,N-dimethylacetamide in an amount of about 10 to 100 times the total amount of the nucleoside and the catalyst at room temperature for about 4 hours to obtain the nucleoside.

A 2,2'-anhydronucleoside can be obtained by reacting a ribonucleoside with thionyl chloride in an amount of 2 mols per mole of the nucleoside in N,N-dimethylacetamide in an amount of about 10 to 100 times the total amount of the nucleoside and the thionyl chloride at about 160° C for about 2 hours. Conversely, the 2,2'-anhydronucleoside can be reacted with hydrous pyridine in an amount of about 10 to 100 times the amount of the nucleoside at about 0° C for about 10 minutes to obtain the corresponding arabinonucleoside.

In the same manner as above an acylnucleoside can be used in place of the nucleoside to obtain a protected derivative of the acylnucleoside and, conversely, the protected nucleoside can be subjected to a hydrolysis or reduction as described above to obtain the acylnucleoside.

An $N^4$-trimethylsilyl-acetylnucleoside can be obtained by reacting an acylnucleoside with trimethylsilyl chloride in an amount of 1.1 mols of the trimethylsilyl chloride per mol of the acylnucleoside in pyridine in an amount of about 10 to 100 times the total amount of the acylnucleoside and the chloride at a temperature of about 5° C for about 20 hours.

A 5'-O-tosyl- or -mesyl-acylnucleoside can be obtained by reacting an $N^4$-acylnucleoside or an $N^4$-trihaloethoxycarbonylacylnucleoside with tosyl chloride or mesyl chloride in an amount of 1.1 mols of the chloride per mol of the nucleoside in pyridine in an amount of about 10 to 100 times the total amount of the nucleoside and the chloride at about 5° C for about 20 hours. A 2'- or 3'-O-tosyl- or -mesylacylnucleoside can be obtained by treating an $N^4$-acyl-5'-O-trityl- or $N^4$-trihaloethoxycarbonyl-5'-O-acyl-, or $N^4$-trihaloethoxy carbonyl-5'-trityl-2'- or 3'-O-acylnucleoside in the same manner as above and subjecting the product to silica gel chromatographic separation.

A 2'-, 3'- or 5'-halo-acylnucleoside can be obtained by reacting the above 2'-, 3'- or 5'-O-tosyl- or -mesyl-acylnucleoside with lithium chloride, lithium bromide or sodium iodide, etc., in an amount of about 10 mols per mol of the nucleoside in N,N-dimethylacetamide in an amount of about 10 to 100 times the total amount of the nucleoside and the lithium chloride, lithium bromide or sodium iodide at room temperature for about 20 hours.

Compound II can be prepared by a combination of one or more of the above procedures from an appropriate nucleoside.

The present invention is further illustrated in greater detail by the following Examples. Unless otherwise indicated, all procedures in the Examples were carried out at atmospheric pressure and at room temperature (about 20°-25° C).

In these Examples, the numerical values of ultraviolet absorptions (UV) indicte the maximum absorptions in the ultraviolet absorption spectrum in terms of mμ as determined in ethanol, and the numerical values of infrared absorptions (IR) indicate characteristic absorptions in the infrared absorption spectrum due to an amido group or an ester group in terms of cm$^{-1}$ as determined by the KBr tablet method.

The numerical values shown after the empirical formula indicte the molecular weight of the indicted product, and the numerical values of the elementary analysis calculated from the empirical formula are indicted in terms of percent, with the found values in parentheses.

EXAMPLE 1

10 mmol of $N^4$-trimethylsilyl-5'-O-{14(2-tetrahydropyranyloxy)myristoyl} cytidine and 11 mmol of terephthalic acid were added to 400 ml of dioxane, and the mixture was stirred for 2 hours. The resulting reaction mixture was then concentrated at 0.2 atm. at a temperature of 50° C. The resulting residue was added to 100 ml of tetrahydrofuran followed by heating at a temperature of 80° C to dissolve the residue. The solution was allowed to cool to room temperature and 100 ml of water was added to the solution. The white precipitate formed was collected by filtration and air-dried to obtain 3.2 mmol (32% yield) of $N^4$-hemiterephthaloyl-5'-O-{14-(2-tetrahydropyranyloxy)myristoyl}cytidine as a white powder.

Elementary Analysis: Calcd. for $C_{36}H_{51}O_{11}N_3$ (701.79): C, 61.61; H, 7.33; N, 5.99. Found: C, 61.73; H, 7.35; N, 5.91.

U.V.: 212, 265, 305 (shoulder).
I.R.: 1735, 1710, 1635, 1178.

EXAMPLE 2

10 mmol of $N^4$-{14-(2-thienyl)myristoyl}-5'-O-p-nitrotoluenesulfonylcytosine arabinoside and 11 mmol of dihydroxytartaric acid were added to 600 ml of acetone, and the mixture was stirred for 3 hours. The resulting reaction mixture was then concentrated at 0.2 atm. at a temperature of 40° C. The resulting residue was added to 100 ml of tetrahydrofuran followed by heating at a temperature of 80° C to dissolve the residue. The solution was allowed to cool to room temperature and 100 ml of water was added to the solution. The white precipitate formed was collected by filtration and air-dried to obtain 2.8 mmol (28% yield) of $N^4$-{14-(2-thienyl)myristoyl}-5'-O-hemidihydroxytartaroyl-cytosine arabinoside as a white powder.

Elementary Analysis: Calcd. for $C_{31}H_{45}O_{13}N_3S_1$ (699.76): C, 53.21; H, 6.48; N, 6.00. Found: C, 53.25; H, 6.52; N, 5.93.

U.V.: 215, 248, 300.
I.R.: 1735, 1710, 1635, 1178.

EXAMPLE 3

10 mmol of $N^4$-cyclohexyllauroyl-3'-methanesulfonyl-5-fluorocytidine and 11 mmol of mercaptosuccinic acid were added to 200 ml of dimethylformamide, and the mixture was stirred for 3 hours. The resulting reaction mixture was then concentrated at 0.2 atm. at a temperature of 60° C. The resulting residue was added to 100 ml of tetrahydrofuran followed by heating at a temperature of 80° C to dissolve the residue. The solution was allowed to cool to room temperature and 100 ml of water was added to the solution. The white precipitate formed was collected by filtration and air-dried to obtain 3.1 mmol (31% yield) of $N^4$-cyclohexyllauroyl-3'-O-hemimercaptosuccinyl-5-fluorocytidine as a white powder.

Elementary Analysis: Calcd. for $C_{31}H_{47}O_9N_3FS$ (656.78): C, 56.59; H, 7.21; N, 6.40. Found: C, 56.74; H, 7.32; N, 6.35.

U.V.: 215, 248, 299
I.R.: 1735, 1710, 1635, 1178.

EXAMPLE 4

10 mmol of $N^4$-trichloroethoxycarbonyl-5'-O-thiophenoxylauroyl-2'-deoxy-2'-bromo-5-chlorocytosine arabinoside and 11 mmol of mucic acid were added to 200 ml of pyridine, and the mixture was stirred for 30 minutes. The resulting reaction mixture was then concentrated at 0.2 atm. at a temperature of 40° C. The resulting residue was added to 100 ml of tetrahydrofuran followed by heating at a temperature of 80° C to dissolve the residue. The solution was allowed to cool to room temperature and 100 ml of water was added to the solution. The white precipitate formed was collected by filtration and air-dried to obtain 3.2 mmol (32% yield) of $N^4$-trichloroethoxycarbonyl-5'-O-thiophenoxylauroyl-2'-O-hemimucoyl-5-chlorocytosine arabinoside.

Elementary Analysis: Calcd. for $C_{36}H_{47}O_{15}N_3Cl_4S$ (935.66): C, 46.21; H, 5.06; N, 4.49. Found: C, 46.28; H, 5.10; N, 4.47.

U.V.: 210, 248, 300.
I.R.: 1735, 1710, 1635, 1180.

EXAMPLE 5

10 mmol of $N^4$-p-nitrophenyllauroyl-5'-deoxy-5'-iodo-5-bromocytidine and 11 mmol of 1,1-cyclobutanedicarboxylic acid disodium salt were added to 600 ml of acetonitrile, and the mixture was stirred for 30 minutes. The resulting reaction mixture was then concentrated at 0.2 atm. at a temperature of 50° C. The resulting was added to 100 ml of tetrahydrofuran followed by heating at a temperature of 80° C to dissolve the residue. The solution was allowed to cool to room temperature and 100 ml of water was added to the solution. The white precipitate formed was collected by filtration and air-dried to obtain 2.9 mmole (29% yield) of $N^4$-p-nitrophenyllauroyl-5'-O-(1-carboxycyclobutanecarbonyl)-5-bromocytidine monosodium salt as a white powder.

Elementary Analysis: Calcd. for $C_{33}H_{42}O_{11}N_4BrNa$ (773.62): C, 51.23 H, 5.47; N, 7.24. Found: C, 51.26; H, 5.51; N, 7.23.

U.V.: 215, 248, 305.
I.R.: 1735, 1710, 1635, 1180.

EXAMPLE 6

10 mmol of 5'-O-triphenylmethyl-3'-O-phenoxylauroyl-2'-deoxy-2'-chloro-5-iodocytosine arabinoside and 11 mmol of 3,4-furandicarboxylic acid dipotassium salt were added to 200 ml of N,N-dimethylacetamide, and the mixture was stirred for 3 hours. The resulting reaction mixture was then concentrated at 0.2 atm. at a temperature of 60° C. The resulting residue was added to 100 ml of tetrahydrofuran followed by heating at a temperature of 80° C to dissolve the residue. The solution was allowed to cool to room temperature and 100 ml of water was added to the solution. The white precipitate formed was collected by filtration and air-dried to obtain 3.2 mmol (32% yield) of 5'-O-triphenylmethyl-3'-O-phenoxylauroyl-2'-O-(4-carboxyfuran-3-carbonyl)-5-iodocytosine arabinoside monopotassium salt as a white powder.

Elementary Analysis: Calcd. for $C_{52}H_{53}O_{11}N_3IK$ (1061.98): C, 58.81; H, 5.03; N, 3.96. Found: C, 58.85; H, 5.06; N, 3.92.

U.V.: 256, 272.
I.R.: 1735, 1180.

EXAMPLE 7

10 mmol of 2',3'-O-dibenzyl-5-bromouridine and 20 mmol of 2-mercaptostearic acid were added to 400 ml of dimethylformamide containing 40 ml of N,N'-dicyclohexylcarbodiimide, and the mixture was stirred for 3 hours. The resulting reaction mixture was then concentrted at 0.2 atm. at a temperature of 60° C. 200 ml of cyclohexane was added to the residue, and the mixture was heated at a temperature of 80° C for 2 hours while refluxing. The reaction mixture was filtered to recover the residue, and the residue was washed three times with cyclohexane. The resulting residue was then added to 100 ml of dimethylformamide followed by heating at a temperature of 80° C to dissolve the residue. The solution was allowed to cool to room temperature and 100 ml of water was added to the solution. The white precipitate formed was collected by filtration and air-dried to obtain 5.6 mmol (56% yield) of 5'-O-(2-mercaptostearoyl)-2',3'-O-dibenzyl-5-bromouridine as a white powder.

Elementary Analysis: Calcd. for $C_{41}H_{57}O_7N_2BrS$ (801.87): C, 61.41; H, 7.16; N, 3.49. Found: C, 61.49; H, 7.21; N, 3.45.

U.V.: 265.
I.R.: 1735, 1180.

EXAMPLE 8

10 mmol of $N^4$-trichloroethoxycarbonyl-3'-O-stearoyl-2,2'-anhydrocytidine and 20 mmol of 1,3-acetonedicarboxylic acid were added to 200 ml of diemthylsulfoxide containing 40 mmol of N-cyclohexyl-N-morpholinoethylcarbodilmide, and the mixture stirred for 2 hours. The resulting reaction mixture was then concentrated at 0.2 atm. at a temperature of 60° C. The resulting residue was added to 400 ml of chloroform, and the mixture was heated at a temperature of 60° C to dissolve the residue. The solution was allowed to stand at room temperature for 20 hours, and the white precipitate formed ws collected by filtration. The precipitate thus obtained was then air-dried to obtain 4.7 mmol (47% yield) of $N^4$-trichloroethoxycarbonyl-5'-O-(3-carboxyacetonecarbonyl)-3'-O-stearoyl-2,2'-anhydrocytidine as a white powder.

Elementary Analysis: Calcd. for $C_{35}H_{50}O_{11}N_3Cl_3$ (795.14): C, 52.86; H, 6.34; N, 5.28. Found: C, 52.91; H, 6.35; N, 5.27.

U.V.: 215, 248, 300
I.R.: 1735, 1710, 1635, 1178

EXAMPLE 9

10 mmol of $N^4$-trichloroethoxycarbonyl-5'-O-oleoyl-2,2'-anhydrocytosine arabinoside and 15 mmol of 1,3-adamantanediacetyl chloride were added to 200 ml of tetramethylurea and the mixture was stirred for 5 minutes at a temperature of 80° C. The resulting reaction mixture was allowed to cool to room temperature, and 10 mmol of pyridine was added thereto. The solution was then concentrated at 0.2 atm. at a temperature of 60° C. The resulting residue was added to 100 ml of benzene followed by heating at a temperature of 80° C for 2 hours while refluxing. The mixture was allowed to cool to room temperature, and the precipitate formed was collected by filtration. The precipitate thus obtained was added to 100 ml of N,N-dimethylformamide followed by heating at 80° C to dissolve the precipitate. The solution was allowed to cool to room temperature, and 100 ml of water was added to the solution. The white precipitate formed was collected by filtration and air-dried to obtain 3.5 mmol (35% yield) of $N^4$-trichloroethoxycarbonyl-5'-O-oleyl-3'-O-(3-carboxymethyladamantane)acetyl-2,2'-anhydrocytosine arabinoside as a white powder.

Elementary Analysis: Calcd. for $C_{44}H_{60}O_{10}N_3Cl_3$ (897.31): C, 58.89; H, 6.74; N, 4.68. Found: C, 58.92; H, 6.75; N, 4.67.

U.V.: 215, 248, 300
I.R.: 1735, 1710, 1635, 1178.

EXAMPLE 10

10 mmol of 5',3'-di-O-tetrahydropyranyl-5-chlorouridine and 20 mmol of arachidonoic anhydride were added to 200 ml of hexamethylphosphoramide, and the mixture was stirred for 4 hours at a temperature of 80° C. The resulting reaction mixture was then concentrated at 0.2 atm. at a temperature of 60° C. 100 ml of toluene was added to the resulting residue followed by heating at a temperature of 80° C while refluxing. The mixture was then allowed to cool to room temperature, and the precipitate formed as collected gy filtration. 200 ml of dioxane was then added to the precipitate and the mixture was heated at a temperature of 80° C to dissolve the residue. The solution was allowed to cool to room temperature, and 100 ml of water was added to the solution. The white precipitate formed was collected by filtration and air-dried to obtain 3.9 mmol (39% yield) of 5',3'-di-O-tetrahydropyranyl-2'-O-arachidonoyl-5-chlorouridine as a white powder.

Elementary Analysis: Calcd. for $C_{39}H_{63}O_9N_2Cl$ (739.37): C, 63,35; H, 8.59; N, 3.79. Found: C, 63.42; H, 8.61; N, 3.75.

U.V.: 267.
I.R.: 1735, 1178.

EXAMPLE 11

10 mmol of $N^4$-(18-hydroxystearoyl)-5-chlorocytosine arabinoside and 20 ml of glutaric anhydride were added to a mixture of 500 ml of dioxane and water (90:10 by volume), and the resulting mixture was allowed to react at a temperature of 80° C for 4 hours. The resulting reaction mixture was poured into 1 liter of ice-water, and the precipitate formed was collected by filtration and air-dried. The dried precipitate was then added to 500 ml of chloroform and the mixture was heated at a temperature of 60° C to dissolve the precipitate. The solution was allowed to cool to room temperature, and the white precipitate formed was collected by filtration and air-dried to obtain 8.5 mmol (85% yield) of $N^4$-(18-hydroxystearoyl)-5'-O-hemiglutaroyl-5-chlorocytidine arabinoside as a white powder.

Elementary Analysis: Calcd. for $C_{32}H_{52}O_{10}N_3Cl$ (674.22): C, 57.00; H, 7.77; N, 6.23. Found: C, 57.17; H, 7.79; N, 6.20.

U.V.: 215, 248, 300.
I.R.: 1735, 1710, 1635, 1178.

EXAMPLE 12

10 mmol of $N^4$-stearoylcytosine arabinoside and 11 mmol of succinic anhydride were added to 100 ml of N,N-dimethylformamide, and the mixture was stirred for 4 hours at a temperature of 80° C. The reaction mixture was allowed to cool to 5° C, and 100 ml of ice-water was added to the mixture. The white precipitate formed was collected by filtration and added to 400 ml of chloroform followed by heating at a temperature of 60° C. The solution was cooled to 5° C and allowed to stand for 20 hours. The white precipitate formed was collected by filtration and air-dried to obtain 6.7 mmol (67% yield) of $N^4$-stearoyl-5'-O-hemisuccinylcytosine arabinoside as a white powder.

Elementary Analysis: Calcd. for $C_{31}H_{51}O_9N_3$ (609.74): C, 61.06; H, 8.43; N, 6.90. Found: C, 60.73; H, 8.38; N, 6.81.

U.V.: 215, 249, 299.
I.R.: 1735, 1710, 1635, 1178.

In the same manner as described in Example 12 but using 10 mmol of N⁴-n-nonadecanoylcytosine arabinoside, 10 mmol of N⁴-arachidoylcytosine arabinoside, 10 mmol of N⁴-n-heneicosanoylcytosine arabinoside, 10 mmol of N⁴-behenoylcytosine arabinoside or 10 mmol of N⁴-palmitoylcytosine arabinoside in place of 10 mmol of the N⁴-stearoylcytosine arabinoside used in Example 12, the following corresponding 5′-hemisuccinyl derivative was obtained in each instance as a white powder:

N⁴-n-nonadecanoyl-5′-O-hemisuccinylcytosine arabinoside (67% yield).

Elemenatary Analysis: Calcd. for $C_{32}H_{53}O_9N_3$ (623.76): C, 61.61; H, 8.56; N, 6.74. Found: C, 61.63; H, 8.61; N, 6.70.

U.V.: 215, 248, 300.

I.R.: 1735, 1710, 1635, 1180.

N⁴-arachidoyl-5′-O-hemisuccinylcytosine arabinoside (65% yield).

Elementary Analysis: Calcd. for $C_{33}H_{55}O_9N_3$ (637.79): C, 62.14; H, 8.69; N, 6.59. Found: C, 62.17; H, 8.71; N, 6.54.

U.V.: 215, 249, 300.

I.R.: 1735, 1710, 1635, 1180.

N⁴-n-heneicosanoyl-5′-O-hemisuccinylcytosine arabinoside (61% yield).

Elementary Analysis: Calcd. for $C_{34}H_{57}O_9N_3$ (641.79): C, 63.63; H, 8.95; N, 6.55. Found: C, 63.68; H, 8.97; N, 6.53.

U.V.: 215, 249, 300.

I.R.: 1735, 1710, 1635, 1180.

N⁴-behenoyl-5′-O-hemisuccinylcytosine arabinoside (67% yield).

Elementary Analysis: Calcd. for $C_{35}H_{59}O_9N_3$ (665.84): C, 63.13; H, 8.93; N, 6.31. Found: C, 63.15; H, 8.97; N, 6.30.

U.V.: 215, 249, 300.

I.R.: 1735, 1710. 1635, 1178.

N⁴-palmitoyl-5′-O-hemisuccinylcytosine arabinoside (64% yield).

Elementary Analysis: Calcd. for $C_{29}H_{47}O_9N_3$ (581.69): C, 59.88; H, 8.15; N, 7.22. Found: C, 59.89; H, 8.21; N, 7.20.

U.V.: 215, 248, 300.

I.R.: 1735, 1710, 1635, 1178.

EXAMPLE 13

In the same manner as described in Example 12 but using 10 mmol of 5-fluorouridine in place of 10 mmol of the N⁴-stearoylcytosine arabinoside, and 11 mmol of palmitic anhydride in place of 11 mmol of the succinic anhydride, 6.1 mmol of 5′-O-palmitoyl-5-fluorouridine was obtained in 61% yield as a white powder.

Elementary Analysis: Calcd. for $C_{25}H_{41}O_7N_2F$ (500.60): C, 59.98; H, 8.26; N, 5.60. Found: C, 59.99; H, 8.31; N, 5.55.

U.V.: 266.

I.R.: 1735, 1178.

In the same manner as described above but using 11 mmol of stearic anhydride, 11 mmol of arachidic anhydride or 11 mmol of behenic anhydride in place of 11 mmol of the palmitic anhydride, the following corresponding 5-fluorouridine derivative was obtained in each instance:

5′-O-stearoyl-5-fluorouridine (63% yield).

Elementary Analysis: Calcd. for $C_{27}H_{45}O_7N_2F$ (528.65): C, 61.34; H, 8.58; N, 5.30. Found: C, 61.39; H, 8.62; N, 5.24.

U.V.: 266.

I.R.: 1735, 1178.

5′-O-arahidoyl-5-fluorouridine (61% yield).

Elementary Analysis: Calcd. for $C_{29}H_{45}O_7N_2F$ (556.70): C, 62.56; H, 8.87; N, 5.03. Found: C, 62.61; H, 8.92; N, 5.01.

U.V.: 266.

I.R.: 1735, 1178.

5′-O-behenoyl-5-fluorouridine (61% yield).

Elementary Analysis: Calcd. for $C_{31}H_{53}O_7N_2F$ (584.75): C, 63.67; H, 9.14; N, 4.79. Found: C, 63.72; H, 9.21; N, 4.76.

U.V.: 266.

I.R.: 1735, 1178.

EXAMPLE 14

In the same manner as described in Example 12 but using 10 mmol of the following 5-fluoro-2′-deoxyuridine in place of 10 mmol of the 5-fluorouridine, the following corresponding 5-fluoro-2′-deoxyuridine derivative was obtained in each instance:

5′-O-palmitoyl-5-fluoro-2′-deoxyuridine (59% yield).

Elementary Analsysis: Calcd. for $C_{25}H_{41}O_6N_2F$ (484.60): C, 61.96; H, 8.53; N, 5.78. Found: C, 62.03; H, 8.55; N, 5.76.

U.V.: 266.

I.R.: 1735, 1180.

5′-O-stearoyl-5-fluoro-2′-deoxyuridine (58% yield).

Elementary Analysis: Calcd. for $C_{27}H_{45}O_6N_2F$ (512.65): C, 63.25; H, 8.85; N, 5.47. Found: C, 63.28; H, 8.91; N, 5.45.

U.V.: 266.

I.R.: 1735, 1180.

5′-O-arachidoyl-5-fluoro-2′-deoxyuridine (57% yield).

Elementary Analysis: Calcd. for $C_{29}H_{49}O_6N_2F$ (540.70). C, 64.41; H, 9.13; N, 5.18. Found: C, 64.52; H, 9.21; N, 5.15.

U.V.: 266.

I.R.: 1735, 1180.

5′-O-behenoyl-5-fluoro-2′-deoxyuridine (59% yield).

Elementary Analysis: Calcd. for $C_{31}H_{53}O_6N_2F$ (568.75): C, 66.23; H, 9.39; N, 4.93. Found: C, 66.29; H, 9.42; N, 4.91.

U.V.: 266.

I.R.: 1735, 1180.

EXAMPLE 15

In the same manner as described in Example 14 but using 10 mmol of 5-iodo-2′-deoxyuridine in place of 10 mmol of the 5-fluoro-2′-deoxyuridine, the following corresponding 5-iodo-2′-deoxyuridine derivative was obtained in each instance:

5′-O-palmitoyl-5-iodo-2′-deoxyuridine (57% yield).

Elementary Analysis: Calcd. for $C_{25}H_{41}O_6N_2I$ (592.52): C, 50.67; H, 6.98; N, 4.73. Found: C, 50.71; H, 7.08; N, 4.72.

U.V.: 266.

I.R.: 1735, 1180.

5′-O-stearoyl-5-iodo-2′-deoxyuridine (54% yield).

Elementary Analysis: Calcd. for $C_{27}H_{45}O_6N_2I$ (620.57): C, 52.25; H, 7.31; N, 4.52. Found: C, 52.39; H, 7.45; N, 4.50.

U.V.: 266.

I.R.: 1735, 1180.

5′-O-arachidoyl-5-iodo-2′-deoxyuridine (55% yield).

Elementary Analysis: Calcd. for $C_{29}H_{49}O_6N_2I$ (648.62): C, 53.70; H, 7.65; N, 4.32. Found: C, 53.78; H, 7.71; N, 4.30.

U.V.: 266.
I.R.: 1735, 1180.

5'-O-behenoyl-5-iodo-2'-deoxyuridine (52% yield).
Elementary Analysis: Calcd. for $C_{31}H_{53}O_6N_2I$ (676.67): C, 55.02; H, 7.89; N, 4.14. Found: C, 55.15; H, 7.81; N, 4.12.
U.V.: 266.
I.R.: 1735, 1180.

EXAMPLE 16

In the same manner as described in Example 12 but using each of 10 mmol of 5'-O-arachidoyl-5-fluoro-2'-deoxyuridine and 10 mmol of 5'-O-behenoyl-5-iodo-2'-deoxyuridine in place of 10 mmol of the $N^4$-stearoylcytosine arabinoside, the following corresponding 3'-O-hemisuccinyl derivative was obtained in each instance:

5'-O-arachidoyl-3'-O-hemisuccinyl-5-fluoro-2'-deoxyuridine (54% yield).
Elementary Analysis: Calcd. for $C_{33}H_{53}O_9N_2F$ (640.77): C, 61.85; H, 8.34; N, 4.37. Found: C, 61.91; H, 8.42; N, 4.35.
U.V.: 266.
I.R.: 1735, 1180.

5'-O-behenoyl-3'-O-hemisuccinyl-5-iodo-2'-deoxyuridine (52% yield).
Elementary Analysis: Calcd. for $C_{35}H_{57}O_9N_2F$ (776.75): C, 54.12; H, 7.40; N, 3.61. Found: C, 54.25; H, 7.52; N, 3.60.
U.V.: 267.
I.R.: 1735, 1180.

EXAMPLE 17

10 mmol of 2'-methoxystearoyluridine and 11 mmol of fumaroyl chloride were added to 30 ml of N,N-dimethylacetamide, and the mixture was stirred for 2 hours at a temperature of 70° C. The resulting mixture was then concentrated at 0.2 atm. at a temperature of 50° C. The resulting residue was dissolved in 100 ml of chloroform at a temperature of 60° C, and the solution was cooled to 5° C. The white precipitate formed was collected by filtration and air-dried to obtain 3.7 mmol (37% yield) of 5'-O-hemifumaroyl-2'-O-methoxystearoyluridine as a white powder.
Elementary Analysis: Calcd. for $C_{32}H_{50}O_{11}N_2$ (638.74): C, 60.17; H, 7.89; N, 4.39. Found: C, 60.27; H, 7.91; N, 4.38.
U.V.: 265.
I.R.: 1735, 1180.

EXAMPLE 18

10 mmol of $N^4$-phenyllauroyl-5-bromocytosine arabinoside and 11 mmol of homophthaloyl azide were added to 100 ml of pyridine and the mixture was stirred for 2 hours at a temperature of 80° C. The resulting reaction mixture was then concentrated at 0.2 atm. at a temperature of 40° C. The resulting residue was added to 200 ml of chloroform followed by heating at 60° C to dissolve the residue. The solution was allowed to cool to 5° C, and the white precipitate formed was collected by filtration. The precipitate thus obtained was air-dried to obtain 3.8 mmol (38% yield) of $N^4$-phenyllauroyl-5'-O-hemiphthaloyl-5-bromocytosine arabinoside as a white powder.
Elementary Analysis: Calcd. for $C_{37}H_{46}O_9N_3Br$ (756.68): C, 58.73; H, 6.13; H, 5.55. Found: C, 58.79; H, 6.15; H, 5.52.
U.V.: 215, 250, 300.
I.R.: 1735, 1710, 1635, 1180.

EXAMPLE 19

10 mmol of 5'-O-heminitrosuccinyl-5-fluoro-2,2'-anhydrocytidine and 40 mmol of 2-behenoyloxy-2-methylpropionyl chloride were added to 20 ml of acetonitrile, and the mixture was heated at a temperature of 80° C for 2 hours. The reaction mixture was then concentrated at 0.2 atm. at a temperature of 60° C. The resulting residue was added to 200 ml of chloroform followed by heating at 60° C to dissolve the residue. The solution was allowed to cool to 5° C, and the precipitate formed was collected by filtration. The resulting precipitate was air-dried to obtain 3.9 mmol (39% yield) of 5'-O-heminitrosuccinyl-3'-O-benhenoyl-5-fluoro-2,2'-anhydrocytidine as a white powder.
Elementary Analysis: Calcd. for $C_{35}H_{55}O_{10}N_4F$ (710.82): C, 59.14; H, 7.80; N, 7.88. Found: C, 59.28; H, 7.82; N, 7.86.
U.V.: 215, 248, 300.
I.R.: 1735, 1180.

In the same manner as described above but using 10 mmol of 2'-deoxyuridine, 10 mmol of 5-chloro-2'-deoxyuridine, 10 mmole of 5-bromo-2'-deoxyuridine or 10 mmol of 5-iodouridine in place of 10 mmol of the 5'-O-heminitrosuccinyl-5-fluoro-2,2'-anhydrocytidine, the following corresponding 3'-O-behenoyl derivative was obtained in each instance:

3'-O-behenoyl-2'-deoxyuridine (32% yield).
Elementary Analysis: Calcd. for $C_{31}H_{54}O_6N_2$ (550.76): C, 67.60; H, 9.88; N, 5.09. Found: C, 67.82; H, 9.89; N, 5.01.
U.V.: 265.
I.R.: 1735, 1180.

3'-O-behenoyl-5-chloro-2'-deoxyuridine (33% yield).
Elementary Analysis: Calcd. for $C_{31}H_{53}O_6N_2Cl$ (585.22): C, 63.63; H, 9.13; N, 4.79. Found: C, 63.72; H, 9.15; N, 4.72.
U.V.: 265.
I.R.: 1735, 1180.

3'-O-behenoyl-5-bromo-2'-deoxyuridine (35% yield).
Elementary Analysis: Calcd. for $C_{31}H_{53}O_6N_2Br$ (629.68): C, 59.13; H, 8.49; N, 4.45. Found: C, 59.29; H, 8.51; N, 4.47.
U.V.: 265.
I.R.: 1735, 1178.

3'-O-behenoyl-5-iodouridine (32% yield).
Elementary Analysis: Calcd. for $C_{31}H_{53}O_6N_2I$ (676.68): C, 55.02; H, 7.90; N, 4.14. Found: C, 55.15; H, 7.93; N, 4.12.
U.V.: 265.
I.R.: 1735, 1178.

EXAMPLE 20

10 mmol of $N^4$-(4-oxostearoyl)-5',3'-O-dibenzyl-5-iodocytidine and 20 mmol of bromosuccinic anhydride were stirred in 100 ml of pyridine at a temperature of 40° C for 2 hours. The resulting reaction mixture was then concentrated at 0.2 atm. at a temperature of 40° C. The resulting residue was suspended in 1 liter of water, and the precipitate was collected by filtration. The solid thus obtained was air-dried, and washed with 500 ml of benzene. The solid was then added to 400 ml of chloroform followed by heating at 60° C to dissolve the solid. The resulting solution was cooled to 5° C and the white precipitate formed was collected by filtration. The precipitate thus obtained was air-dried to obtain 3.7 mmol (37% yield) of $N^4$-(4-oxostearoyl)-5',3'-dibenzyl-2'-O-hemibromosuccinyl-5-iodocytidine as a white powder.

Elementary Analysis: Calcd. for $C_{45}H_{59}O_{10}N_3IBr$ (1008.78): C, 53.57; H, 5.90; N, 4.17. Found: C, 53.69; H, 5.92; N, 4.15.
U.V.: 215, 250, 300.
I.R.: 1735, 1710, 1635, 1180.

EXAMPLE 21

10 mmol of $N^4$-stearoyl-5'-deoxy-5'-iodocytosine arabinoside and 20 mmol of tartaric acid were added to 200 ml of N,N-dimethylacetamide, and 200 ml of trimethylamine was then added slowly to the mixture while stirring. The resulting reaction mixture was stirred for 1.5 hours at a temperature of 80° C and allowed to cool to 5° C. Then, 20% hydrochloric acid cooled to 5° C was added to the reaction mixture until the pH of the mixture reached 7.0. The precipitate formed was collected by filtration and added to 200 ml of chloroform followed by heating at 60° C to dissolve the precipitate. The solution was cooled to 5° C, and the precipitate formed was collected by filtration and air-dried to obtain 5.2 mmol of $N^4$-stearoyl-5'-O-hemitartaroylcytosine arabinoside as a white powder.

In the same manner as described above but using each of 20 mmol of p-phenylenediacetic acid, 20 mmol of L-N-carbobenzyloxyaspartic acid, 20 mmol of 1,1-cyclohexanediacetic acid, 10 mmol of diglycolic acid, 10 mmol of itaconic acid, 10 mmol of 2,5-pyridinedicarboxylic acid, 10 mmol of chloromaleic acid or 10 mmol of dithioglycolic acid in place of 20 mmol of the tartaric acid, the following corresponding $N^4$-stearoyl derivative was obtained in each instance:

$N^4$-stearoyl-5'-O-hemitartaroylcytosine arabinoside (52% yield).
Elementary Analysis: Calcd. for $C_{31}H_{51}O_{11}N_3$ (641.74): C, 58.02; H, 8.01; N, 6.55. Found: C, 58.19; H, 8.09; N, 6.52.
U.V.: 215, 248, 300.
I.R.: 1735, 1710, 1635, 1178.

$N^4$-stearoyl-5'-O-(4-carboxymethylphenyl)acetylcytosine arabinoside (36% yield).
Elementary Analysis: Calcd. for $C_{37}H_{55}O_9N_3$ (685.83): C, 64.77; H, 8.08; N, 6.12. Found: C, 64.58; H, 8.05; N, 6.10.
U.V.: 215, 250, 300.
I.R.: 1735, 1710, 1635, 1180.

$N^4$-stearoyl-5'-O-N-carbobenzyloxyaspartoyl)cytosine arabinoside (32% yield).
Elementary Analysis: Calcd. for $C_{39}H_{57}O_{11}N_4$ (757.88): C, 61.80; H, 7.58; N, 7.39. Found: C, 61.89; H, 7.63; N, 7.34.
U.V.: 215, 248, 300.
I.R.: 1735, 1710, 1635, 1180.

$N^4$-stearoyl-5'-O-(1-carboxymethylcyclohexyl)acetylcytosine arabinoside (33% yield).
Elementary Analysis: Calcd. for $C_{37}H_{59}O_9N_3$ (689.86): C, 64.41; H, 8.62; N, 6.69. Found: C, 64.57; H, 8.65; N, 6.62.
U.V.: 215, 248, 300.
I.R.: 1735, 1710, 1635, 1178.

$N^4$-stearoyl-5'-O-hemidiglycoloylcytosine arabinoside (31% yield).
Elementary Analysis: Calcd. for $C_{31}H_{51}O_{10}N_3$ (625.74): C, 59.50; H, 8.22; N, 6.72. Found: C, 59.67; H, 8.29; N, 6.70.
U.V.: 215, 248, 300.
I.R.: 1735, 1710, 1635, 1180.

$N^4$-stearoyl-5'-O-hemiitaconoylcytosine arabinoside (28% yield).

Elementary Analysis: Calcd. for $C_{32}H_{51}O_9N_3$ (621.75): C, 61.81; H, 8.27; N, 6.76. Found: C, 61.99; H, 8.31; N, 6.74.
U.V.: 215, 248, 300.
I.R.: 1735, 1710, 1635, 1180.

$N^4$-stearoyl-5'-O-(5-carboxypyridine-3-carbonyl)cytosine arabinoside (33% yield).
Elementary Analysis: Calcd. for $C_{34}H_{50}O_9N_4$ (658.77): C, 61.96; H, 7.65; N, 8.49. Found: C, 61.92; H, 7.69; N, 8.45.
U.V.: 215, 252, 300.
I.R.: 1735, 1710, 1635, 1180.

$N^4$-stearoyl-5'-O-hemichloromaleoylcytosine arabinoside (32% yield).
Elementary Analysis: Calcd. for $C_{31}H_{49}O_9N_3$ (607.72): C, 61.26; N, 8.12; N, 6.91. Found: C, 61.39; H, 8.15; N, 6.85.
U.V.: 215, 248, 300.
I.R.: 1735, 1710, 1635, 1180.

$N^4$-stearoyl-5'-O-hemidithioglycoloylcytosine arabinoside (31% yield).
Elementary Analysis: Calcd. for $C_{31}H_{51}O_9N_3S$ (641.80): C, 58.01; H, 8.01; N, 6.55. Found: C, 58.17; H, 8.09; N, 6.54.
U.V.: 215, 248, 300.
I.R.: 1735, 1710, 1635, 1180.

EXAMPLE 22

10 mmol of 5'-O-(16-carboxymethylpalmitoyl)-5-fluoro-2,2'-anhydrocytidine hydrochloride and 20 mmol of 1-glutaroylimidazole were added to 200 ml of tetrahydrofuran, and the mixture was stirred at a temperature of 60° C for 20 hours. The resulting reaction mixture was poured into 1 liter of ice-water and, after stirring the mixture, the precipitate formed was collected by filtration. The resulting solid was added to 400 ml of chloroform followed by heating at 60° C to dissolve the solid. The solution was cooled to 5° C and the white precipitate formed was collected by filtration and air-dried to obtain 3.5 mmol of 5'-O-(16-carboxymethylpalmitoyl)-3'-O-hemiglutaryl-5-fluoro-2,2'-anhydrocytidine hydrochloride.

In the same manner as described above, each of 10 mmol of 5'-O-(18-thiomethoxystearoyl)-5-chloro-2,2'-anhydrocytidine hydrochloride, 10 mmol of 5'-O-(12,13-epoxy-9-octadecanoyl)-5-bromo-2,2'-anhydrocytidine hydrochloride, and 10 mmol of 5'-O-behenoyl-5-iodo-2,2'-anhydrocytidine hydrochloride was used in place of 10 mmol of the 5'-O-(16-carboxymethylpalmitoyl)-5-fluoro-2,2'-anhydrocytidine hydrochloride to obtain the following corresponding 3'-O-glutaryl derivative:

5'-O-(16-carboxymethylpalmitoyl)-3'-O-hemiglutaryl-5-fluoro-2,2'-anhydrocytidine monohydrochloride salt (35% yield).
Elementary Analysis: Calcd. for $C_{32}H_{49}O_{10}N_3FCl$ (690.19): C, 55.68; H, 7.16; N, 6.09. Found: C, 55.77; H, 7.21; N, 6.04.
U.V.: 215, 248, 300.
I.R.: 1735, 1710, 1635, 1180.

5'-O-(18-thiomethoxystearoyl)-3'-O-hemiglutaryl-5-chloro-2,2'-anhydrocytidine monohydrochloride salt (30% yield).
Elementary Analysis: Calcd. for $C_{33}H_{53}O_8N_3Cl_2S$ (722.74): C, 54.84; H, 7.39; N, 5.81. Found: C, 54.97; H, 7.41; N, 5.76.
U.V.: 215, 248, 300.
I.R.: 1735, 1710, 1635, 1180.

5'-O-(12,13-epoxy-9-octadecanoyl)-3'-0-hemiglutaryl-5-bromo-2,2'-anhydrocytidine monohydrochloride salt (29% yield).

Elementary Analysis: Calcd. for $C_{32}H_{49}O_9N_3BrCl$ (735.11): C, 52.28; H, 6.72; N, 5.72. Found: C, 52.36; H, 6.81; N, 5.70.

U.V.: 215, 248, 300.

I.R.: 1735, 1710, 1635, 1180.

5'-O-behenoyl-3'-hemiglutaryl-5-iodo-2,2'-anhydrocytidine monohydrochloride salt (30% yield).

Elementary Analysis: Calcd. for $C_{36}H_{59}O_8N_3ICl$ (824.23): C, 52.46; H, 7.22; N, 5.10. Found: C, 52.51; H, 7.25; N, 5.10.

U.V.: 215, 248, 300.

I.R.: 1735, 1710, 1635, 1180.

EXAMPLE 23

10 mmol of $N^4$-(2-chlorostearoyl)cytidine arabinoside and 11 mmol of cyanoethylcitraconoyl were stirred in 100 ml of N,N-dimethylacetamide at a temperature of 60° C for 20 hours. The resulting reaction mixture was then concentrated at 0.2 atm. at a temperature of 40° C. The resulting residue was added to 300 ml of chloroform followed by heating at 60° C to dissolve the residue. The solution was allowed to cool to 5° C, and the white precipitate formed was collected by filtration and air-dried to obtain 2.4 mmol (24% yield) of $N^4$-(2-chlorostearoyl)-5'-O-hemicitraconoylcytosine arabinoside as a white powder.

Elementary Analysis: Calcd. for $C_{31}H_{54}O_9N_3Cl$ (648.22): C, 57.44; H, 8.40; N, 6.48. Found: C, 57.46; H, 8.52; N, 6.42.

U.V.: 215, 248, 300.

I.R.: 1735, 1710, 1635, 1178.

EXAMPLE 24

10 mmol of sodium bicarbonate was added to 600 ml of an ethanolic solution of 10 mmol of $N^4$-stearoyl-5'-O-hemisuccinylcytosine arabinoside followed by stirring of the mixture at a temperature of 60° C to dissolve the sodium bicarbonate. The resulting transparent solution was concentrated at 0.2 atm. at a temperature of 40° C, and the resulting residue was immediately freeze-dried to obtain 10 mmol of $N^4$-stearoyl-5'-O-hemisuccinylcytosine arabinoside sodium salt as a white powder.

In the same manner as described above, 10 mmol of $N^4$-hemiterephthaloyl-5'-O-{14-(2-tetrahydropyranyloxy)myristoyl}-cytidine and 10 mmol of potassium bicarbonate; 10 mmol of $N^4$-{14-(2-thienyl)-myristoyl}-5'-O-hemidihydroxytartaroylcytidine arabinoside and 10 mmol of ammonium bicarbonate; 10 mmol of $N^4$-cyclohexyllauroyl-3'-O-hemimercaptosuccinyl-5-fluorocytidine and 10 mmol of trimethylammonium bicarbonate; 10 mmol of $N^4$-(18-hydroxystearoyl)-5'-O-hemiglutaroyl-5-chlorocytosine arabinoside and 10 mmol of triethylammonium bicarbonate; 10 mmol of $N^4$-stearoyl-5'-O-hemisuccinylcytosine arabinoside and 10 mmol of procaine carbonate; 10 mmol of 5'-O-hemifumaroyl-2'-O-methoxystearoyluridine and 10 mmol of dibenzylammonium bicarbonate; 10 mmol of $N^4$-phenyllauroyl-5'-O-hemiphthaloyl-5-bromocytosine arabinoside and 10 mmol of N-benzyl-$\beta$-phenethylammonium bicarbonate; 10 mmol of $N^4$-stearoyl-5'-O-hemitartaroylcytosine arabinoside and 10 mmol of choline carbonate; 10 mmol of 5'-O-arachidoyl-3'-O-hemisuccinyl-5-fluoro-2'-deoxyuride and 5 mmol of calcium carbonate; or 10 mmol of 5'-O-behenoyl-3'-O-hemisuccinyl-5-iodo-2'-deoxyuridine and 5 mmol of N,N'-dibenzylethylenediammonium bicarbonate were used to obtain the following alkali metal, alkaline earth metal, ammonium or substituted ammonium salt in each instance. These salts were found to be soluble in water in a proportion of 1 to 10 mg of the salt/ml of water.

$N^4$-stearoyl-5'-O-hemisuccinylcytosine arabinoside sodium salt, $N^4$-hemiterephthaoloyl-5'-{14-(2-tetrahydropyranyloxy)myristoyl}cytidine potassium salt, $N^4$-{14-(2-thienyl)myristoyl}-5'-O-hemidihydroxytartaroylcytosine arabinoside ammonium salt, $N^4$-cyclohexyllauroyl-3'-O-hemimercaptosuccinyl-5-fluorocytidine trimethylammonium salt, $N^4$-(18-hydroxystearoyl)-5'-O-hemiglutaroyl-5-chlorocytosine arabinoside triethylammonium salt, $N^4$-stearoyl-5'-O-hemisuccinylcytosine arabinoside procaine salt, 5'-O-hemifumaroyl-2'-O-methoxystearoyluridine dibenzylammonium salt, $N^4$-phenyllauroyl-5'-O-hemiphthaloyl-5-bromocytosine arabinoside N-benzyl-$\beta$-phenethylammonium salt, $N^4$-stearoyl-5'-O-hemitartaroylcytosine arabinoside choline salt, 5'-O-arachidoyl-3'-O-hemisuccinyl-5-fluoro-2'-deoxyuridine calcium salt, and 5'-O-behenoyl-3'-O-hemisuccinyl-5-iodo-2'-deoxyuridine N,N'-dibenzylethylene diammonium salt.

EXAMPLE 25

In order to investigate the increase of life span (an improvement of survival rate in leukemia mice) brought about by the novel compounds of this invention in L-1210 leukemia mice, 100,000 L-1210 leukemia cells per mouse were transplanted by intraperitoneal injection into $CDF_1$ female mice (10 mice per group), and, two and six days after the transplantation, each of the test compounds indicated below was administered to the mice by intraperitoneal injection at a dosage level of 100 mg/kg or 200 mg/kg (body weight). All of the test compounds were administered as a suspension in physiological saline solution containing 1% Tween 80. The same physiological saline solution containing no test compounds was also intraperitoneally administered to identical groups of mice in the same manner as above as a control.

The activity of each of the test compounds for increasing the life span in the leukemia mice was indicated in terms of $T/C \times 100$ (%) where "T" designates the mean survival time of the group treated with the test compound and "C" designates the mean survival time of the control group.

The two numerical values in the parenthesis shown after the test compounds shown below are T/C (%) values at dosage levels of 100 mg/kg (1st value) and 200 mg/kg (2nd value), respectively. The value 100 indicates no effectiveness and a value higher than 100 is considered to be effective.

$N^4$-hemiterephthaloyl-5'-O-{14-(2-tetrahydropyranyloxy)myristoyl}cytidine sodium salt (100, 160), $N^4$-hemiterephthaloyl-5'-O-{14-(2-tetrahydropyranyloxy)myristoyl}cytosine arabinoside sodium salt (190, 240), $N^4$-{14-(2-thienyl)myristoyl}-5'-O-hemidihydroxytartaroylcytosine arabinoside sodium salt (190, 240), $N^4$-cyclohexyllauroyl-3'-O-hemimercaptosuccinyl-5-fluorocytidine sodium salt (150, 200), 5'-O-thiophenoxylauroyl-2'-O-hemimucoyl-5-chlorocytosine arabinoside sodium salt (140, 190),
N⁴-p-nitrophenyllauroyl-5'-O-(1-carboxycyclobutanecarbonyl)-5-bromocytidine sodium salt (140, 190),
3'-O-phenoxylauroyl-2'-O-(4-carboxyfuran-3-carbonyl)-5-iodocytosine arabinoside potassium salt (130, 180),
5'-O-(2-mercaptostearoyl)-5-bromouridine (180, 150),
5'-O-(3-carboxyacetonecarbonyl)-3'-O-stearoyl-2,2'-anhydrocytidine (100, 200),
5'-O-oleoyl-3'-O-(3-carboxymethyladamantane)acetyl-2,2'-anhydrocytosine arabinoside (100, 200),
2'-O-arachidonoyl-5-chlorouridine (170, 100),
N⁴-(18-hydroxystearoyl)-5'-O-hemiglutaroyl-5-chlorocytosine arabinoside sodium salt (190, 240),
N⁴-stearoyl-5'-O-hemisuccinylcytosine arabinoside sodium salt (230, 280),
N⁴-n-nonadecanoyl-5'-O-hemisuccinylcytosine arabinoside sodium salt (230, 280),
N⁴-arachidoyl-5'-O-hemisuccinylcytosine arabinoside sodium salt (220, 280),
N⁴-n-heneicosanoyl-5'-O-hemisuccinylcytosine arabinoside sodium salt (220, 280),
N⁴-behenoyl-5'-O-hemisuccinylcytosine arabinoside sodium salt (220, 280),
N⁴-palmitoyl-5'-O-hemisuccinylcytosine arabinoside sodium salt (150, 200),
5'-O-palmitoyl-5-fluorouridine (170, 180),
5'-O-stearoyl-5-fluorouridine (170, 180),
5'-O-arachidoyl-5-fluorouridine (170, 180),
5'-O-behenoyl-5-fluorouridine (170, 180),
5'-O-palmitoyl-5-fluoro-2'-deoxyuridine (160, 170),
5'-O-stearoyl-5-fluoro-2'-deoxyuridine (160, 170),
5'-O-arachidoyl-5-fluoro-2'-deoxyuridine (160, 170),
5'-O-behenoyl-5-fluoro-2'-deoxyuridine (160, 170),
5'-O-palmitoyl-5-iodo-2'-deoxyuridine (100, 150),
5'-O-stearoyl-5-iodo-2'-deoxyuridine (100, 150),
5'-O-arachidoyl-5-iodo-2'-deoxyuridine (100, 150),
5'-O-behenoyl-5-iodo-2'-deoxyuridine (100, 150),
5'-O-arachidoyl-3'-O-hemisuccinyl-5-fluoro-2'-deoxyuridine sodium salt (100, 180),
5'-O-behenoyl-3'-O-hemisuccinyl-5-iodo-2'-deoxyuridine sodium salt (100, 170),
5'-O-hemifumaroyl-2'-O-methoxystearoyluridine sodium salt (100, 140),
N⁴-phenyllauroyl-5'-O-hemiphthaloyl-5-bromocytosine arabinoside sodium salt (190, 240),
5'-O-heminitrosuccinyl-3'-O-behenoyl-5-fluoro-2,2'-anhydrocytidine (100, 150),
3'-O-behenoyl-2'-deoxyuridine (100, 100),
3'-O-behenoyl-5-chloro-2'-deoxyuridine (150, 130),
3'-O-behenoyl-5-bromo-2'-deoxyuridine (140, 150),
3'-O-behenoyl-5-iodo-2'-deoxyuridine (140, 150),
N⁴-(4-oxostearoyl)-2'-O-hemibromosuccinyl-5-iodocytidine sodium salt (130, 140),
N⁴-stearoyl-5'-O-hemitartaroylcytosine arabinoside sodium salt (190, 240),
N⁴-stearoyl-5'-O-(4-carboxymethylphenyl)acetylcytosine arabinoside sodium salt (190, 240),
N⁴-stearoyl-5'-O-(L-N-carbobenzyloxyaspartoyl)cytosine arabinoside sodium salt (180, 200),
N⁴-stearoyl-5'-O-(1-carboxymethylcyclohexyl)acetylcytosine arabinoside sodium salt (190, 240),
N⁴-stearoyl-5'-O-hemidiglycoloylcytosine arabinoside sodium salt (190, 230),
N⁴-stearoyl-5'-O-hemiitaconylcytosine arabinoside sodium salt (190, 220),
N⁴-stearoyl-5'-O-(5-carboxypyridine-3-carbonyl)cytosine arabinoside sodium salt (190, 220),
N⁴-stearoyl-5'-O-hemichloromaleoylcytosine arabinoside sodium salt (190, 230),
N⁴-stearoyl-5'-O-hemidithioglycoloylcytosine arabinoside sodium salt (190, 200),
5'-O-(16-carboxymethylpalmitoyl)-3'-O-hemiglutaryl-5-fluoro-2,2'-anhydrocytidine hydrochloride salt (150, 140).

While the invention has been described in detail with reference to specific embodiments thereof, it will be apparent to one skilled in the art that various changes and modifications can be made therein without departing the spirit and the scope thereof.

What is claimed is:

1. A compound selected from the group consisting of compounds represented by the general formulae

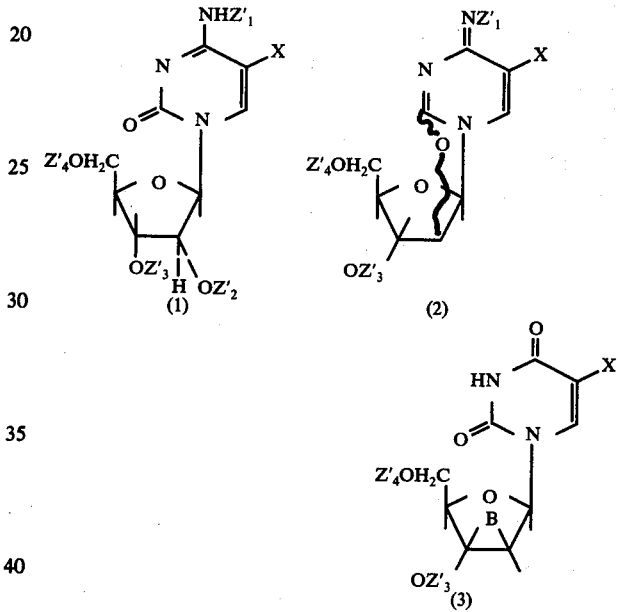

wherein
(a) B represents $OZ_2'$ or hydrogen;
(b) one of $Z_1'$, $Z_2'$, $Z_3'$ and $Z_4'$ represents $A_1$ and another represents $A_2$ and the remainder represents hydrogen or a protective group wherein
$A_1$ is $C_{14}$-$C_{22}$ aliphatic acyl selected from the group consisting of myristoyl, palmitoyl, margaroyl, stearoyl, n-nonadecanoyl, arachidoyl, n-heneicosanoyl, behenoyl, oleoyl, arachidonoyl, or the aliphatic acyl substituted with fluoro, chloro, bromo, iodo, hydroxy, mercapto, phenyl, phenoxy, thiophenoxy, nitrophenyl, cyclohexyl, 2-thienyl, 2-tetrahydropyranyloxy, methoxy, thiomethoxy, carboxymethyl, epoxy and oxo;
$A_2$ is $C_2$-$C_{14}$ having carboxy or the acyl substituted with a group selected from the group consisting of phenyl, hydroxy, fluoro, chloro, bromo, iodo, N-carbobenzyloxyamino, cyclohexyl, mercapto, nitro, furane, pyridine, oxo, adamantane, oxymethenylcarboxy and thiomethenylcarboxy; and
the protective group is selected from the group consisting of isopropylidene, ethylidene, benzylidene, tetrahydropyranyl, tetrahydrofuranyl, ethoxyethyl, methoxymethyl, ethoxymethyl, methoxyethyl, triphenylmethyl, 2,4-dinitroanilino, methoxycarbonyl, trichloroethoxycarbonyl, tribromoethoxycarbonyl, formyl, trifluoroacetyl, trichloroacetyl, benzyl, benzhydrine, 2,4-dinitrophenylsulphenyl, propenyl, borate, vinylthioether and benzoylpropyl; and (c) X is selected from the group consisting of hydrogen, fluorine, chlorine, bromine and iodine;
and pharmaceutically acceptable salts thereof.

2. A compound according to claim 1, wherein said compound is selected from the group consisting of compounds represented by formula (1), (2) and pharmaceutically acceptable salts thereof.

3. A compound according to claim 1, wherein said compound is selected from the group consisting of compounds represented by formula (2) and pharmaceutically acceptable salts thereof.

4. A compound according to claim 1 wherein said compound is selected from the group consisting of compounds represented by formula (2) and pharmaceutically acceptable salts thereof, and wherein $Z_1'$ is $A_1$, $Z_4'$ is $A_2$, and $Z_3'$ is hydrogen.

5. A compound according to claim 1, wherein the pharmaceutically acceptable salt is selected from the group consisting of a sodium salt, a potassium salt, a calcium salt, an ammonium salt, a trimethylamine salt, a triethylamine salt, a procaine salt, a dibenzylamine salt, N-benzyl-β-phenylamine salt, N,N'-dibenzylethylenediamine salt and a chloline salt.

6. A compound according to claim 5, wherein
(a) $A_1$ is selected from the group consisting of myristoyl, palmitoyl, margaroyl, stearoyl, n-nonadecanoyl, arachidoyl, n-heneicosanoyl, behenoyl, oleoyl, arachidonoyl, 2-chlorostearoyl, 18-hydroxystearoyl, 2-mercaptostearoyl, phenylauroyl, phenoxylauroyl, p-nitrophenyllauroyl, thiophenoxylauroyl, cyclohexyllauroyl, 14-(2-thienyl)myristoyl, 14-(2-tetrahydropyranyloxy)myristoyl, 18-methoxystearoyl, 18-thiomethoxystearoyl, 16-carboxymethylpalmitoyl, 12,13-epoxy-9-octadecanoyl and 4-oxostearoyl; and (b) $A_2$ is selected from the group consisting of hemifumaroyl, 4-carboxymethylphenylacetyl, hemitartroyl, hemiterephthaloyl, hemisuccinyl, hemicitraconoyl, hemihomophthaloyl, hemibromosuccinyl, hemi-N-carbobenzyloxy-L-aspartyl, 1'-carboxymethylcyclohexylacetyl, hemidiglycoloyl, hemihydroxytartroyl, hemiitaconyl, hemiglutaryl, hemimercaptosuccinyl, hemimucoyl, heminitrosuccinyl, 1-carboxycyclobutanecarbonyl, 4-carboxyfurane-3-carbonyl, 5-carboxypyridine-2-carbonyl, 3-carboxyacetonecarbonyl, 3-carboxymethyladamataneacetyl, hemichloromaleoyl and hemidithioglycoloyl.

7. A compound according to claim 1 wherein
(a) $A_1$ is selected from the group consisting of myristoyl, palmitoyl, margaroyl, stearoyl, n-nonadecanoyl, arachidoyl, n-heneicosanoyl and behenoyl;
(b) $A_2$ is hemisuccinyl;
(c) X is hydrogen of fluorine; and
(d) the pharmaceutically acceptable salt is a sodium salt.

8. A compound according to claim 1, wherein
(a) $A_1$ is selected from the group consisting of myristoyl, palmitoyl, margaroyl, stearoyl, n-nonadecanoyl, arachidoyl, n-heneicosanoyl and behenoyl;
(b) $A_2$ is hemisuccinyl; and
(c) the pharmaceutically acceptable salt is a sodium salt.

* * * * *